United States Patent
Steineger et al.

(10) Patent No.: US 11,911,354 B2
(45) Date of Patent: *Feb. 27, 2024

(54) SUBSTITUTED FATTY ACIDS FOR TREATING NON-ALCOHOLIC STEATOHEPATITIS

(71) Applicant: BASF AS, Oslo (NO)

(72) Inventors: Hilde Steineger, Oslo (NO); David Alan Fraser, Blommenholm (NO); Tore Skjæret, Oslo (NO)

(73) Assignee: BASF, Oslo (NO)

( * ) Notice: Subject to any disclaimer, the term of this patent is extended or adjusted under 35 U.S.C. 154(b) by 0 days.

This patent is subject to a terminal disclaimer.

(21) Appl. No.: 17/551,673

(22) Filed: Dec. 15, 2021

(65) Prior Publication Data
US 2022/0280459 A1 Sep. 8, 2022

Related U.S. Application Data

(63) Continuation of application No. 16/532,633, filed on Aug. 6, 2019, now Pat. No. 11,234,948, which is a continuation of application No. 16/177,108, filed on Oct. 31, 2018, now Pat. No. 10,722,481, which is a continuation of application No. 15/567,334, filed as application No. PCT/EP2016/058909 on Apr. 21, 2016, now abandoned.

(30) Foreign Application Priority Data

Apr. 28, 2015 (NO) .................................... 20150514

(51) Int. Cl.
| | | |
|---|---|---|
| A61K 31/10 | (2006.01) | |
| C07C 321/18 | (2006.01) | |
| A61K 31/19 | (2006.01) | |
| A61K 31/22 | (2006.01) | |
| A61P 1/16 | (2006.01) | |

(52) U.S. Cl.
CPC .............. *A61K 31/19* (2013.01); *A61K 31/22* (2013.01); *A61P 1/16* (2018.01)

(58) Field of Classification Search
CPC .............................. A61K 31/10; C07C 321/18
USPC .......................................... 514/713; 554/101
See application file for complete search history.

(56) References Cited

U.S. PATENT DOCUMENTS

| | | |
|---|---|---|
| 2,909,554 A | 10/1959 | Doerr |
| 4,009,211 A | 2/1977 | Onopchenko et al. |
| 4,032,564 A | 6/1977 | Henrick et al. |
| 4,040,781 A | 8/1977 | Lamberti et al. |
| 4,209,410 A | 6/1980 | Baldwin |
| 4,214,088 A | 7/1980 | Abeler et al. |
| 4,286,053 A | 8/1981 | Ishikawa et al. |

(Continued)

FOREIGN PATENT DOCUMENTS

| | | |
|---|---|---|
| CA | 2115345 | 2/1993 |
| CA | 2667211 | 5/2008 |

(Continued)

OTHER PUBLICATIONS

2014 Therapeutic Area Partnerships meeting website; meeting dates: Nov. 19-21, 2014; Boston, MA; original website: http://www.iirusa.com/therapeuticareapartnership/home.xml; accessible via the internet archives at https://archive.org/web:https://web.archive.org/web/20141220122529/http:/www.iirusa.com/therapeuticareapartnership/home.XML (3 pages).

(Continued)

*Primary Examiner* — Douglas M Willis
(74) *Attorney, Agent, or Firm* — FINNEGAN, HENDERSON, FARABOW, GARRETT & DUNNER, LLP

(57) ABSTRACT

The present disclosure relates to a method of preventing and/or treating non-alcoholic steatohepatitis in a subject in need thereof, comprising administering to the subject a pharmaceutically effective amount of a compound of Formula (II):

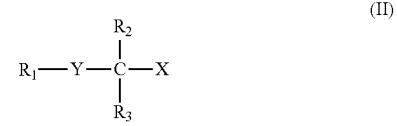

wherein $R_1$, R2, R3, X and Y are as defined in the specification;
or a pharmaceutically acceptable salt, solvate, or solvate of such a salt.

More particularly, the present disclosure relates to a method of preventing and/or treating non-alcoholic steatohepatitis in a subject in need thereof, comprising administering to the subject a pharmaceutically effective amount of a compound of Formula (I):

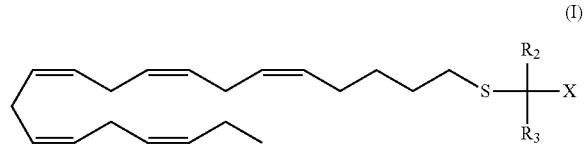

wherein R2, $R_3$, and X, are as defined in the specification;
or a pharmaceutically acceptable salt, solvate, or solvate of such a salt.

Further, the present invention relates to a compound of Formula (I) for preventing and/or treating non-alcoholic steatohepatitis, wherein $R_2$, $R_3$ and X are as defined in the specification; or a pharmaceutically acceptable salt, solvate, or solvate of such a salt.

20 Claims, 4 Drawing Sheets

(56) References Cited

U.S. PATENT DOCUMENTS

| | | | |
|---|---|---|---|
| 4,297,268 A | 10/1981 | Abeler et al. | |
| 4,368,190 A | 1/1983 | Shen et al. | |
| 4,411,808 A | 10/1983 | Gutierrez et al. | |
| 4,444,766 A | 4/1984 | Bosies et al. | |
| 4,652,441 A | 3/1987 | Okada et al. | |
| 5,306,754 A | 4/1994 | Yamamoto et al. | |
| 5,328,953 A | 7/1994 | Lynch | |
| 5,445,832 A | 8/1995 | Orsolini et al. | |
| 5,447,820 A | 9/1995 | Hayakawa et al. | |
| 5,523,430 A | 6/1996 | Patel et al. | |
| 5,612,093 A | 3/1997 | Braig et al. | |
| 5,763,517 A | 6/1998 | Yamamoto et al. | |
| 5,770,584 A | 6/1998 | Kucera et al. | |
| 5,990,173 A | 11/1999 | Patoiseau et al. | |
| 6,060,515 A | 5/2000 | Elias et al. | |
| 6,365,628 B1 | 4/2002 | Berge | |
| 6,376,688 B1 | 4/2002 | Ferrante et al. | |
| 6,511,670 B1 | 1/2003 | Maignan et al. | |
| 6,624,190 B2 | 9/2003 | Khoury et al. | |
| 6,723,717 B1 | 4/2004 | Youngquist et al. | |
| 7,250,456 B2 | 7/2007 | Eigen et al. | |
| 7,273,852 B2 | 9/2007 | Tsuji et al. | |
| 7,427,583 B2 | 9/2008 | Couillet et al. | |
| 7,517,858 B1 | 4/2009 | Hostetler et al. | |
| 7,902,399 B2 | 3/2011 | Berge et al. | |
| 7,968,617 B2 | 6/2011 | Thalacker et al. | |
| 8,173,831 B2 | 5/2012 | Milne et al. | |
| 8,304,551 B2 | 11/2012 | Milne et al. | |
| 8,735,436 B2 | 5/2014 | Hovland et al. | |
| 8,741,966 B2 | 6/2014 | Holmeide | |
| 8,759,558 B2 | 6/2014 | Holmeide et al. | |
| 9,394,228 B2 | 7/2016 | Hovland et al. | |
| 10,722,481 B2 | 7/2020 | Steineger | |
| 11,234,948 B2 | 2/2022 | Steineger | |
| 2003/0147814 A1 | 8/2003 | Scherrer et al. | |
| 2004/0126424 A1 | 7/2004 | Jandacek et al. | |
| 2005/0107503 A1 | 5/2005 | Couillet et al. | |
| 2006/0135785 A1 | 6/2006 | Patoiseau et al. | |
| 2006/0247458 A1 | 11/2006 | Yamamoto et al. | |
| 2007/0060497 A1 | 3/2007 | Krahmer et al. | |
| 2007/0008170 A1 | 4/2007 | Bryhn et al. | |
| 2007/0167529 A1 | 7/2007 | Walton et al. | |
| 2007/0254862 A1 | 11/2007 | Antel et al. | |
| 2009/0137567 A1 | 5/2009 | Perrine et al. | |
| 2010/0267828 A1 | 10/2010 | Holmeide et al. | |
| 2010/0280109 A1 | 11/2010 | Holmeide | |
| 2011/0190395 A1 | 8/2011 | Holmeide et al. | |
| 2012/0122940 A1 | 5/2012 | Hovland et al. | |
| 2012/0252850 A1 | 10/2012 | Milne et al. | |
| 2012/0264791 A1 | 10/2012 | Milne et al. | |
| 2013/0046013 A1 | 2/2013 | Hovland et al. | |
| 2013/0172244 A1 | 7/2013 | Klein et al. | |
| 2013/0295173 A1 | 11/2013 | Machielse et al. | |
| 2013/0345269 A1 | 12/2013 | Hovland et al. | |
| 2014/0221439 A1 | 8/2014 | Hovland et al. | |
| 2014/0316002 A1 | 10/2014 | Holmeide et al. | |
| 2016/0206585 A1 | 7/2016 | Hustvedt | |
| 2018/0110747 A1 | 4/2018 | Fraser | |
| 2019/0314304 A1 | 10/2019 | Steineger | |
| 2020/0085772 A1 | 3/2020 | Steineger | |
| 2021/0177794 A1 | 6/2021 | Steineger et al. | |

FOREIGN PATENT DOCUMENTS

| | | |
|---|---|---|
| CA | 2667150 | 11/2008 |
| CN | 1248916 A | 3/2000 |
| CN | 101213281 A | 7/2008 |
| CN | 101225064 | 7/2008 |
| CN | 101213281 B | 3/2013 |
| EA | 023207 | 5/2016 |
| EP | 0 002 007 | 5/1979 |
| EP | 0 050 327 | 4/1982 |
| EP | 0 175 591 | 3/1986 |
| EP | 0 399 183 | 11/1990 |
| EP | 0 463 947 | 1/1992 |
| EP | 2147910 A1 | 1/2010 |
| EP | 2 248 798 | 11/2010 |
| GB | 1038723 | 8/1966 |
| GB | 1523276 | 8/1978 |
| JP | 48-039001 B | 11/1973 |
| JP | 04-051149 | 2/1992 |
| JP | 11-180929 | 7/1999 |
| JP | 2000-344736 A | 12/2000 |
| JP | 2003-527364 T | 9/2003 |
| JP | 2012-526094 | 10/2012 |
| JP | 2014-505017 | 2/2014 |
| WO | WO 97/38688 | 10/1997 |
| WO | WO 98/32444 | 7/1998 |
| WO | WO 99/16804 | 4/1999 |
| WO | WO 00/072920 | 12/2000 |
| WO | WO 01/68582 | 9/2001 |
| WO | WO 01/098328 | 12/2001 |
| WO | WO 03/014073 | 2/2003 |
| WO | WO 03/063878 | 8/2003 |
| WO | WO 2005/073164 | 8/2005 |
| WO | WO 2006/025246 | 3/2006 |
| WO | WO 2006/044391 | 4/2006 |
| WO | WO 2006/094915 | 9/2006 |
| WO | WO 2006/117664 A1 | 11/2006 |
| WO | WO 2006/117668 A1 | 11/2006 |
| WO | WO 2007/116027 | 10/2007 |
| WO | WO 2008/053331 | 5/2008 |
| WO | WO 2008/053340 | 5/2008 |
| WO | WO 2008/125241 | 10/2008 |
| WO | WO 2009/056983 | 5/2009 |
| WO | WO 2009/061208 | 5/2009 |
| WO | WO 2009/147125 | 12/2009 |
| WO | WO 2009/149496 | 12/2009 |
| WO | WO 2009/156621 | 12/2009 |
| WO | WO 2010/006085 | 1/2010 |
| WO | WO 2010/008299 | 1/2010 |
| WO | WO 2010/128401 | 11/2010 |
| WO | WO 2011/089529 | 7/2011 |
| WO | WO 2012/059818 | 5/2012 |
| WO | WO 2012/115695 | 8/2012 |
| WO | WO 2013/016531 | 1/2013 |
| WO | WO 2013/169797 | 11/2013 |
| WO | WO 2014/045293 | 3/2014 |
| WO | WO 2014/057522 | 4/2014 |
| WO | WO 2014/118097 | 8/2014 |
| WO | WO 2014/132134 A1 | 9/2014 |
| WO | WO 2015/157697 | 10/2015 |
| WO | WO 2016/156912 | 10/2016 |
| WO | WO 2019/111048 | 6/2019 |

OTHER PUBLICATIONS

Ahmad, J et al., "Reactions in Monolayers: Base-Catalyzed Ester Hydrolysis Revisited," *Langmuir* (1990) 6:1797-1799.

Ban, S. et al., "Structure-based design, synthesis, and nonalcoholic steatohepatitis (NASH)-preventive effect of phenylpropanoic acid peroxisome proliferator-activated receptor (PPAR) α-selective agonists," *Bioorganic and Medicinal Chemistry*, (2011) vol. 19, Issue 10, p. 3183-3191.

Belikov, V.G., "Farmazevti'cheskaya khimiya," Moscov, *Vyshaya shcola*, 1993, p. 43-47 (9 pages, including title and copyright pages).

Berge et al., "Metabolic effects of thia fatty acids." *Current Opinion in Lipidology.* 2002; 13(3): 295-330.

Berge, S.M. et al., "Pharmaceutical Salts," *J. Pharmaceutical Sciences* (1977) 66(1):1-19.

Brain, E.G. et al., "Derivatives of 6-Aminopenicillanic Acid. Part II.* Trisubstituted Acetyl Derivatives," *J. Chemical* Society(1962) 1445-1453.

Burness, D.M. "Decarboxylation of Thietin Salts," *J. Organic Chemistry*, (1959) 24(6):849-852.

Cao, G. Selected topics of pharmaceutical chemistry. *China Medical Science Press*, 1993. pp. 123-125.

Chen, et al. Basic Drug Design, 1st Edition (*Huazhong University of Science and Technology (HUST) Press*, 1995), p. 165.

Derzhinskii, AR. et al., "Functional Sulfur-Containing Compounds. 4. Preparation of Chloro(Bromo) Alkyl Sulfones by Oxidative

(56) References Cited

OTHER PUBLICATIONS

Halogenation of Hydroxyalkyl Sulfides and Sulfoxides with Mixtures of Hydrogen Peroxide and a Hydrohalic Acid," *Bulletin of the Academy of Sciences of the* USSR (1982) 31(5):995-1001. Translated from Russian.
English language abstract for CN 101225064.
English language abstract for EP 0 463 947.
English language abstract for JP 04-051149.
English machine translation of JP 11-180929.
English translation. Cao, G. Selected topics of pharmaceutical chemistry. *China Medical Science Press,* 1993. pp. 123-125.
English translation, Chen, et al. Basic Drug Design, 1st Edition (*Huazhong University of Science and Technology (HUST) Press,* 1995), p. 162-169.
English translation of JP 48-039001 B.
English translation. Silverman, R.B., The Organic Chemistry of Drug Design and Drug Action, $2^{nd}$ Edition, 19-20, (*Chemical Industry Press,* 2008).
English Translation, Zeinalov, B.K., "Synthesis and Investigation of Esters of Alkyl Selenium Ethanols," *Azerbajdzanskij Chimiceskij Zurnal* (1981) 5:41-43.
Eriksson, J. et al., "Effects of dapagliflozin and n-3 carboxylic acids on non-alcoholic fatty liver disease in people with type 2 diabetes: a double-blind randomized placebo-controlled study," (2018), 61:1923-1934.
Ferrell, W.J. et al., "Synthesis and Properties of $^{35}$,S, $^{14}$C and $^{3}$H Labeled S-Alkyl Glycerol Ethers and Derivatives," *Chemistry & Physics of Lipids* (1976) 16:276-284.
Ferrucci, L. et al., "Relationship of Plasma Polyunsaturated Fatty Acids to Circulating Inflammatory Markers," J. Clin. Endocrin. & Metab. (2006) 91(2):439-446.
Fliegner, D. et al., "Up-regulation of PPAR-gamma in myocardial infarction," *The European Journal of Heart Failure,* 10 (2008) 30-38.
Flock, S. et al., "Syntheses of Some Polyunsaturated Sulfur- and Oxygen-containing Fatty Acids Related to Eicosapentaenoic and Docosahexaenoic Acids," *Acta Chemica Scandinavica* (1999) 53:436-445.
Francque, S. et al., "PPARa gene expression correlates with severity and histological treatment response in patients with non-alcoholic steatohepatitis," *Journal of Hepatology,* (2015) vol. 63, p. 164-173.
Fuchs, C.D., et al., "Hepatocyte-specific deletion of adipose triglyceride lipase (ATGL/PNPLA2) ameliorates dietary induced steatohepatitis in mice," *Hepatology,* (2021), Accepted Author Manuscript, doi:10.1002/hep.32112.
Geleijnse, J.M. et al., "Blood Pressure Response to Fish Oil Supplementation: Metaregression Analysis of Randomized Trials," *J. Hypertension* (2002) 20(8):1493-1499.
Goldsworthy, L.J. et al., "Some Sulphides Containing the 2-Chloroethyl Group," *J. Chemical* Society (1948) 2177-2179.
Granlund, L. et al., "Effects of Structural Changes of Fatty Acids on Lipid Accumulation in Adipocytes and Primary Hepatocytes," *Biochemica et Biophysica Acta* (2005) 1687:23-30.
Grupp, I.L. et al., "Protection Against Hypoxia-Reoxygenation in the Absence of Poly (ADP-Ribose) Synthetase in Isolated Working Hearts," *J. Mol. Cell Cardiol.* (1999) 31:297-303.
Heckmann, B. et al., "Grignard Additions to $\alpha_1\beta$-Unsaturated Dioxolanones: Preparation of Chiral Allylic Alcohols and Protected $\alpha$-Hydroxy Aldehydes," *Tetrahedron Letters* (1996) 37:1421-1424.
Hermetter, A. & Paltauf, F., "A Facile Procedure for the Synthesis of Saturated Phosphatidylcholines," *Chemistry & Physics of Lipids* (1981) 28:111-115.
Hernandez, V. A. et al., "Thiazolidinediones and Risk of Heart Failure in Patients with or at High Risk or Type 2 Diabetes Mellitus," *Am J Cardiovasc Drugs* 2011; 11(2) pp. 115-128.
Hill, A.J. & Fager, E.W., "Some $\alpha$-Alkylthio Aliphatic Acids," *J. American Chemical Society* (1943) 65(12):2300-2301.
Holmeide, AK. & Skattenbol, L., "Syntheses of Some Polyunsaturated Trifluoromethyl Ketones as Potential Phospholipase $A_2$ Inhibitors," J. Chem. Soc., Perkin Trans. (2000) 1:2271-2276.

Hosokawa, M. et al., "Preparation of Therapeutic Phospholipids Through Porcine Pancreatic Phospholipase $A_2$-Mediated Esterification and Lipozyme-Mediated Acidolysis," *J. Am. Oil Chem. Soc.* (1995) 72(11):1287-1291.
Hsu, W.H. et al., "Monascin and ankaflavin act as natural AMPK activators with PPAR$\alpha$ agonist activity to down-regulate nonalcoholic steatohepatitis in high-fat diet-fed C57BL/6 mice," *Food and Chemical Toxicology,* (2014) vol. 64, p. 94-103.
"Icosabutate for the treatment of hypertriglyceridemia and mixed dyslipidaemia," Nonconfidential Presentation distributed via e-mail by Applicant no earlier than Oct. 7, 2014 (21 pages).
"Icosabutate for the treatment of hypertriglyceridemia and mixed dyslipidaemia," Presentation, Therapeutic Area Partnering meeting in Boston, MA; Nov. 21, 2014 (12 pages).
International Search Report for International Application No. PCT/IB2010/001251, dated Oct. 4, 2010.
International Search Report for International Application No. PCT/IB2011/000250, dated May 31, 2011.
International Search Report for International Application No. PCT/IB2011/002925, dated Mar. 5, 2012.
International Search Report for International Application No. PCT/IB2015/001316, dated Dec. 7, 2015 (3 pages).
International Search Report for International Application No. PCT/NO2008/000391, dated Feb. 4, 2009.
International Search Report for International Application No. PCT/NO2009/000262, dated Oct. 23, 2009.
International Search Report for International Application No. PCT/EP2016/058909, dated Jun. 24, 2016 (11 pages).
International Search Report for International Application No. PCT/IB2018/001459, dated Mar. 8, 2019.
Jones, P.B. et al., "A New Class of Antituberculosis Agents," *J. Med. Chem.* (2000) 43:3304-3314.
Jordan, V.C., "Tamoxifen: a most unlikely pioneering medicine," *Nat Rev Drug Discov;* 2003: 2(3): 205-13.
Kameyama, E. et al., "Alkylcarboxymethyl Sulphoxides," *American Chemical Society Chemical Abstracts* (1971) 74(23):401.
Kasai, Y. et al., "Synthesis of Diphenylalkane Sulfonate and Its Surface Activity," *Kogyo Kagaku Zasshi* (1965) 68(11):2073-2077.
Kholodov, L.E. et al., "Klint'cheskaya farmakokinetika," Moscov, Medicina, 1985, p. 83-98, 134-138, 160, 378-380 (28 pages, including title and copyright pages).
Lam et al., Therapeutic Advances in Gastroenterology, 3(2), 2010, 121-137.
Lamango, N.S et al., "Inhibition Mechanism of S-Adenosylmethionine-Induced Movement Deficits by Prenylcysteine Analogs," *Pharmacology, Biochemistry, & Behavior* (2003) 76:433-442.
Larsen, L.N. et al., "$\alpha$- and $\beta$-Alkyl-Substituted Eicosapentaenoic Acids: Incorporation into Phospholipids and Effects on Prostaglandin H Synthase and 5-Lipoxygenase," *Biochemical Pharmacology* (1998) 55:405-411.
Larsen, L.N. et al., "Polyunsaturated Thia- and Oxa-Fatty Acids: Incorporation into Cell-Lipids and Their Effects on Arachidonic Acid- and Eicosanoid Syntheses," *Biochimica et Biophysica Acta* (1997) 1348:346-354.
Larsen, L.N. et al., "Sulfur-Substituted and $\alpha$-Methylated Fatty Acids as Peroxisome Proliferator-Activated Receptor Activators," *Lipids* (2005) 40(1):49-57.
Lilja-Hallberg, M. & Härröd, M., "Enzymatic Esterification of Long Polyunsaturated Fatty Acids and Lyso-Phosphatidylcholine in Isooctane and Ethanol," *Biocatalysis* (1994) 9:195-207.
Livingston, J.R. & Drogin, R., "The Synthesis and Some Surface Active Properties of Alkylthioalkyl and Alkoxyalkyl Sulfates," *J. American Oil Chemists' Society* (1965) 42:720-723.
Masson, M. et al., "Marine Lipids for Prodrugs, Soft Compounds and Other Pharmaceutical Applications," *Pharmazie* (2000) 55(3):172-177.
Masterton, G.S., et al., "Review article: omega-3 fatty acids—a promising novel therapy for non-alcoholic fatty liver disease," *Aliment Pharmacol Ther,* 2010; 31(7): 679-692.
Matsumoto, M. et al., "Orally Administered Eicosapentaenoic Acid Reduces and Stabilizes Atherosclerotic Lesions in ApoE-Deficient Mice," *Atherosclerosis* (2008) 197:524-533.

(56) References Cited

OTHER PUBLICATIONS

Meyer, K.L. et al., "In Vitro Evaluation of Phosphocholine and Quaternary Ammonium Containing Lipids as Novel Anti-HIV Agents," *J. Med. Chem.* (1991) 34(4):1377-1383.
Notice of Allowance in U.S. Appl. No. 12/741,890, dated Jan. 17, 2014.
Notice of Allowance in U.S. Appl. No. 13/054,212, dated Jan. 29, 2014.
Notice of Allowance in U.S. Appl. No. 13/319,101, dated Jan. 13, 2014.
Notice of Allowance in U.S. Appl. No. 13/883,405, dated Mar. 14, 2016.
Nystrom, R.F. & Brown, W.G., "Reduction of Organic Compounds by Lithium Aluminum Hydride. II. Carboxylic Acids," *J. American Chemical Society* (1947) 69(10):2548-2549.
Office Action from U.S. Appl. No. 12/741,890, dated Aug. 3, 2012.
Office Action from U.S. Appl. No. 12/741,890, dated Dec. 10, 2012.
Office Action from U.S. Appl. No. 12/741,890, dated Aug. 6, 2013.
Office Action from U.S. Appl. No. 13/054,212, dated Apr. 1, 2013.
Office Action from U.S. Appl. No. 13/054,212, dated Jul. 1, 2013.
Office Action from U.S. Appl. No. 13/319,101, dated Jan. 31, 2013.
Office Action from U.S. Appl. No. 13/319,101, dated Apr. 24, 2013.
Office Action from U.S. Appl. No. 13/319,101, dated Oct. 2, 2013.
Office Action (Restriction Requirement) for U.S. Appl. No. 13/574,132 dated Jan. 20, 2015.
Office Action dated Jul. 17, 2014, from U.S. Appl. No. 13/883,405.
Office Action dated Jan. 28, 2015, from U.S. Appl. No. 13/883,405.
Office Action (Restriction Requirement) for U.S. Appl. No. 14/263,793 dated Mar. 3, 2015.
Office Action for U.S. Appl. No. 14/263,793 dated Aug. 11, 2015.
Office Action for U.S. Appl. No. 16/177,108 dated Oct. 8, 2019.
Oh (*Management of Hypertriglyceridemia, American Family Physician*, May 1, 2007, vol. 75, No. 9, pp. 1365-1371).
Okoronkwo, A.E. et al., "Synthesis of ω-Hydroxy-α-Alkyl/Aryl-y-Organo-Selenium and y-Organo-Tellurium: A New Class of Organochalcogen Compounds with Antinociceptive Activity," *Tetrahedron Letters* (2008) 49:3252-3256.
Parkkari, T. et al., "a-Methylated Derivatives of 2-Arachidonoyl Glycerol: Synthesis, CB1 Receptor Activity, and Enzymatic Stability," *Bioorg. & Med. Chem. Lett.* (2006) 16:2437-2440.
Pitt, M.J. et al., "Synthesis of Polyunsaturated β-Oxa Fatty Acids Via Rhodium Mediated Carbenoid Insertion," *Synthesis* (1997) 7:1240-1242.
Qin, Y. et al., "Phase Ib Study of Icosabutate, a Novel Structurally Enhanced Fatty Acid, in Subjects with Hypercholesterolemia," *Circulation;* Nov. 25, 2014; 130(Suppl. 2): A11889; Originally published Nov. 14, 2014 (8 pages).
Qin, Y. et al., "Phase Ib Study of Icosabutate, a Novel Structurally Enhanced Fatty Acid, in Subjects with Hypercholesterolemia," Poster Presentation, *American Heart Association Scientific Sessions,* Chicago, IL, Nov. 17, 2014 (3 pages).
Raspé, E. et al., "Identification of Rev-erbα as a physiological repressor of apoC-III gene transcription[1]," *Journal of Lipid Research,* 2002 43: 2172-2179.
Registry Copyright 2008 ACS on STN (RN 785712-42-7, 714185-72-5, 45247-37-8).
Ringbom, T. et al., "COX-2 Inhibitory Effects of Naturally Occurring and Modified Fatty Acids," *J. Nat. Prod.* (2001) 64:745-749.
Rossmeisl, M. et al., "Prevention and Reversal of Obesity and Glucose Intolerance in Mice by DHA Derivatives," *Obesity* (2009) 17(5):1023-1031.
Sanyal, A.J. et al., EPE-A Study Group, Gastroenterology Aug. 2014;147(2):377-84.e1. doi:10.1053/j. gastro.2014.05.046. Epub May 9, 2014).
Sanyal, A.J., et al. "No Significant Effects of Ethyl-Eicosapentanoic Acid on Histologic Features of Nonalcoholic Steatohepatitis in a Phase 2 Trial," *Gastroenterology,* (2014), vol. 147, No. 2, pp. 377-384.

Scorletti, E. et al., "Effects of purified eicosapentaenoic & docosahexanoic acids in non-alcoholic fatty liver disease: Results from the WELCOME study," Hepatology 2014, Jul. 4 1).
Shchepin, R. et al., "Quorum Sensing in *Candida albicans:* Probing Farnesol's Mode of Action with 40 Natural and Synthetic Farnesol Analogs," *Chemistry & Biology* (2003) 10:743-750.
Shirley, D.A. et al., "Alkylation with Long Chain p-Toluenesulfonates. IV. Alkylation of Alcohols and Amines with n-Octadecyl p-Toluenesulfonate," *J. Organic Chemistry* (1953) 18:378-381.
Silverman, R.B., The Organic Chemistry of Drug Design and Drug Action 4, 14-28 (*Academic Press* 1992).
Silverman, R.B., The Organic Chemistry of Drug Design and Drug Action, $2^{nd}$ Edition, 19-20, (*Chemical Industry Press,* 2008).
Simopoulos, AP., "Essential Fatty Acids in Health and Chronic Disease," *Am. J. Clin. Nutr.* (1999) 70(Suppl):560S-569S.
Srisiri, W. et al., "Syntheses of Polymerizable Monoacylglycerols and 1,2-Diacyl-sn-Glycerols," *J. Org. Chem.* (1996) 61(16):5911-5915.
Stahl, P.H. & Wermuth, C.G., eds., "Chapter 12: Monographs on Acids and Bases" 265-327, in *Handbook of Pharmaceutical Salts: Properties, Selection, and Use.*
Storlien, L.H. et al., "Polyunsaturated Fatty Acids, Membrane Function and Metabolic Diseases Such as Diabetes and Obesity," *Curr. Opin. Clin. Nutr. & Metab. Care* (1998) 1(6):559-563.
Supplementary European Search Report for European Patent Application No. 11 83 7647, dated Feb. 13, 2014.
Togashi, N. et al., "Antibacterial Activity of Long-Chain Fatty Alcohols Against *Staphylococcus aureus,*" *Molecules* (2007) 12:139-148.
Tran, P.O.T. et al., "Inhibition of Interleukin-1β-Induced COX-2 and EP3 Gene Expression by Sodium Salicylate Enhances Pancreatic Islet β-Cell Function," *Diabetes* (2002) 51:1772-1778.
Tsotinis, A. et al., "Synthesis and Antiretroviral Evaluation of New Alkoxy and Aryloxy Phosphate Derivatives of 3'-Azido-3'-Deoxythymidine," *J. Med. Chem.* (1996) 39:3418-3422.
Tungsubutra (Achievement of LDL-cholesterol goal with statins after an ST segment elevation myocardial infarction, *Journal Med Assoc Thai,* Feb. 2005, 98(2), pp. 129-136 (abstract only).
U.S. Appl. No. 16/177,108, Non-Final Office Action dated Oct. 8, 2019, (37 pages).
U.S. Appl. No. 16/177,108, Notice of Allowance dated Apr. 21, 2020, including Examiner Interview Summary, (14 pages).
U.S. Appl. No. 16/532,633, Non-Final Office Action dated Jun. 29, 2020, (13 pages).
U.S. Appl. No. 16/532,633, Final Office Action dated Jan. 26, 2021, (14 pages).
U.S. Appl. No. 16/532,633, Notice of Allowance dated Nov. 22, 2021, (13 pages).
Udding, J. et al., "Xanthate Transfer Cyclization of Glycolic Acid-Derived Radicals. Synthesis of Five- to Eight-Membered Ring Ethers," *J. Org. Chem.* (1994) 59:6671-6682.
Vaagenes, H. et al., "Methylated Eicosapentaenoic Acid and Tetradecylathioacetic Acid: Effects on Fatty Acid Metabolism," *Biochem. Pharmacol.* (1999) 58:1133-1143.
Vippagunta, S.R., et al., "Crystalline solids," *Adv Drug Deliv Rev,* 2001; 48(1): 3-26. (parent).
Wang, P. et al., "Synthesis of Phospholipid-Inhibitor Conjugates by Enzymatic Transphosphatidylation with Phospholipase D," *J. Am. Chem. Soc.* (1993) 115:10487-10491.
Weizmann, C., et al., "The Synthesis of α-Alkoxyisobutyric Acids and Alkyl Methacrylates from Acetonechloroform," *J. Am. Chem. Soc.* (1948) 70:1153-1158.
Willumsen, N. et al., "Enhanced Hepatic Fatty Acid Oxidation and Upregulated Carnitine Palmitoyltransferase II Gene Expression by Methyl β-Thiaoctadeca-6,9,12,15-Tetraenoate in Rats," *J. Lipid Mediators Cell Signaling* (1997) 17:115-134.
Willumsen, N. et al., "On the Effect of 2-Deuterium- and 2-Methyl-Eicosapentaenoic Acid Derivatives on Triglyerides, Peroxisomal 3-Oxidation and Platelet Aggregation in Rats," *Biochimica et Biophysica Acta* (1998) 1369:193-203.
Woodbury, D.M. & Fingl, E., "Chapter 13: Drugs Effective in the Therapy of the Epilepsies," in *Basis of Therapeutics* 201-226 (5th Ed. 1975).

(56) References Cited

OTHER PUBLICATIONS

Wouters, K. et al., "A central role for cholesterol metabolism and inflammation during the inhibition of non-alcoholic steatohepatitis with a synthetic PPARα agonist," *Chemistry and Physics of Lipids*, (2008) vol. 154, Supplement, p. S56.

Written Opinion of the International Searching Authority for International Application No. PCT/IB2015/001316 (7 pages).

Yamaguchi, K. et al., "Inhibiting Triglyceride Synthesis Improves Hepatic Steatosis but Exacerbates Liver Damage and Fibrosis in Obese Mice with Nonalcoholic Steatohepatitis," (2007), vol. 45, No. 6, 1366-1374.

Yan, J. et al., "Omega-3 polyunsaturated fatty acid supplementation and non-alcoholic fatty liver disease: A meta-analysis of randomized controlled trials," *Medicine*, (2018), 97:37, pp. 1-10.

Zeinalov, B.K. et al., "Synthesis and Investigation of Esters of Alkyl Selenium Ethanols," *Azerbajdzanskij Chimiceskij Zumal* (1981) 5:41-43.

Arulanandan, A. et al., "Non-invasive Testing for NASH and NASH with Advanced Fibrosis: Are We There Yet?" Current Hepatology Reports, 2015, 14(2) 109-118.

Chedid A. et al., "The Immunology of Fibrogenesis in Alcoholic Liver Disease" *Arch Pathol Lab Med*, 2004, vol. 128, 1230-1238.

Kim, Y. et al., "Increased Transforming Growth Factor-beta1 in Alcohol Dependence" *J Korean Med Sci*, 2009, 24, 941-944.

Mulder, P. et al., "Macrovesicular steatosis is associated with development of lobular inflammation and fibrosis in diet-induced non-alcoholic steatohepatitis (NASH)" *Inflammation & Cell Signaling*, 2015, vol. 2, 10 pages.

Wang et al., "Exendin-4 decreases liver inflammation and atherosclerosis development simultaneously by reducing macrophage infiltration," British Journal of Pharmacology, 2014, vol. 171, pp. 723-735.

Xu, F. et al., "SIRT1 Mediates the Effect of GLP-1 Receptor Agonist Exenatide on Ameliorating Hepatic Steatosis" *Diabetes*, (2014), 63:3637-3646.

SUBSTITUTED FATTY ACIDS FOR TREATING NON-ALCOHOLIC STEATOHEPATITIS

This application is a continuation U.S. patent application Ser. No. 16/532,633, filed Aug. 6, 2019, which is a continuation of U.S. patent application Ser. No. 16/177,108, filed Oct. 31, 2018, which issued as U.S. Pat. No. 10,722,481 on Jul. 28, 2021, which is a continuation of U.S. patent application Ser. No. 15/567,334, filed Oct. 17, 2017, which is a national stage entry of International Application No. PCT/EP2016/058909, filed Apr. 21, 2016, which claims benefit of priority to Norway Application No. 20150514, filed Apr. 28, 2015, all of which are incorporated herein by reference.

FIELD OF THE INVENTION

The present disclosure relates to a method of preventing and/or treating non-alcoholic steatohepatitis in a subject in need thereof, comprising administering to the subject a pharmaceutically effective amount of a compound of Formula (II):

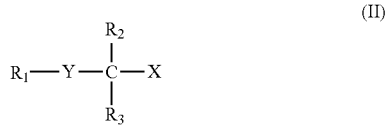

(II)

wherein
$R_1$ is selected from a $C_{10}$-$C_{22}$ alkenyl having 3-6 double bonds;
$R_2$ and $R_3$ are the same or different and may be selected from a group of substituents consisting of a hydrogen atom, a hydroxy group, an alkyl group, a halogen atom, an alkoxy group, an acyloxy group, an acyl group, an alkenyl group, an alkynyl group, an aryl group, an alkylthio group, an alkoxycarbonyl group, a carboxy group, an alkylsulfinyl group, an alkylsulfonyl group, an amino group, and an alkylamino group, provided that $R_2$ and $R_3$ cannot both be a hydrogen atom; or $R_2$ and $R_3$ can be connected in order to form a cycloalkane like cyclopropane, cyclobutane, cyclopentane or cyclohexane;
Y is selected from sulphur, sulfoxide, and sulfone;
X represents a carboxylic acid or a derivative thereof, wherein the derivative is a carboxylic ester, a glyceride, a carboxamide or a phospholipid;
or a pharmaceutically acceptable salt, solvate, or solvate of such a salt.

The present disclosure relates to a method of preventing and/or treating non-alcoholic steatohepatitis in a subject in need thereof, comprising administering to the subject a pharmaceutically effective amount of a compound of Formula (I):

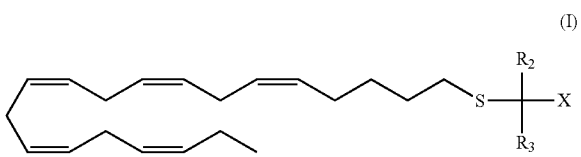

(I)

wherein $R_2$ and $R_3$ are independently chosen from the group of a hydrogen atom and linear, branched, and/or cyclic $C_1$-$C_6$ alkyl groups, with the proviso that $R_2$ and $R_3$ are not both hydrogen; X represents a carboxylic acid or a derivative thereof, wherein the derivative is a carboxylic ester, a glyceride, a carboxamide or a phospholipid; or a pharmaceutically acceptable salt, solvate, or solvate of such a salt.

Further, the present invention discloses compounds of the formulas (I) and (II) for therapeutic and/or prophylactic treatment of non-alcoholic steatohepatitis.

BACKGROUND OF THE INVENTION

Dietary polyunsaturated fatty acids (PUFAs), including omega-3 fatty acids, have effects on diverse physiological processes impacting normal health and chronic diseases, such as the regulation of plasma lipid levels, cardiovascular and immune functions, insulin action, neuronal development, and visual function.

Omega-3 fatty acids, e.g. (5Z,8Z, 11Z, 14Z,17Z)-icosa-5,8,11, 14, 17-pentaenoic acid (EPA) and (4Z,7Z,10Z,13Z,16Z,19Z)-docosa-4,7,10,13,16,19-hexaenoic acid (DHA), regulate plasma lipid levels, cardiovascular and immune functions, insulin action, and neuronal development, and visual function. Omega-3 fatty acids have been shown to have beneficial effects on the risk factors for cardiovascular diseases, for example hypertension and hypertriglyceridemia (HTG).

The use of omega-3 compounds such as EPA and DHA to treat non-alcoholic steatohepatitis (NASH) have been suggested in the prior art. By way of example, WO 2014/057522 of Mochida relates to compositions comprising ethyl icosapentate for use in treatment or alleviation of symptoms of NASH.

Dignity Science LTD (WO2014/118097) have suggested the use of modified omega-3 compounds, such as 15-hydroxy eicosapentaenoic acid (15-OHEPA), to treat fatty liver disorders, such as non-alcoholic fatty liver disease (NAFLD) and non-alcoholic steatohepatitis (NASH). Krisani Biosciences (WO2014/045293) have also proposed the use of modified omega-3 compounds for treating different diseases including non-alcoholic steatohepatitis.

Non-alcoholic fatty liver disease (NAFLD) and non-alcoholic steatohepatitis (NASH) are frequently used interchangeably despite the fact that NAFLD encompasses a much broader spectrum of liver disease including simple hepatosteatosis (>5% of hepatocytes histologically). Hepatosteatosis is most likely a relatively benign disorder when not accompanied by an inflammatory response and cellular damage. However, a subgroup of NAFLD patients have liver cell injury and inflammation in addition to hepatosteatosis, a condition known as nonalcoholic steatohepatitis (NASH). NASH is virtually indistinguishable histologically from alcoholic steatohepatitis (ASH). While the simple steatosis seen in NAFLD does not correlate with increased short-term morbidity or mortality, NASH dramatically increases the risks of cirrhosis, liver failure, and hepatocellular carcinoma (HCC). Cirrhosis due to NASH is an increasingly frequent reason for liver transplantation. While the morbidity and mortality from liver causes are greatly increased in patients with NASH, they correlate even more strongly with the morbidity and mortality from cardiovascular disease.

Uniform criteria for diagnosing and staging NASH are still debated (see details in later sections). Key histologic components of NASH are steatosis, hepatocellular ballooning, and lobular inflammation; fibrosis is not part of the histologic definition of NASH. However, the degree of fibrosis on liver biopsy (stage) is predictive of the prognosis, whereas the degree of inflammation and necrosis on liver biopsy (grade) are not.

With respect to the various histological components, treatment with omega-3 fatty acids have been shown to effectively reduce hepatosteatosis in patients with NAFLD (Scorletti E, et al., Effects of purified eicosapentaenoic and docosahexanoic acids in non-alcoholic fatty liver disease: Results from the *WELCOME study, Hepatology. 2014 Jul. 4 1) and, if treatment is established at an early stage of the disease, may conceivably slow progression to the latter more severe stages of disease. However, it is questionable whether omega-3 fatty acids are sufficiently potent to treat and/or reverse NASH where pronounced histological/inflammatory changes have developed (Sanyal A J, et al; EPE-A Study Group, Gastroenterology. 2014 August; 147(2):377-84.e1. doi: 10.1053/j.gastro.2014.04.046. Epub 2014 May 9).

The moderate efficacy of omega-3 fatty acids in the treatment of NASH may be secondary to their mild effects upon other pathways that underlie the pathogenesis of NASH. Research in both humans and animal models of NASH have convincingly demonstrated that there are multiple factors involved in the development of steatohepatitis as opposed to isolated hepatosteatosis. These include insulin resistance, oxidative stress, inflammation, gut-derived endotoxin and excessive hepatic cholesterol and bile acids. All these factors have been shown to play important contributing factors in genetically susceptible individuals and drugs targeting these pathways are being developed for the treatment of NASH.

The efficacy of synthetic farnesoid X receptor (FXR) agonists, such as obeticholic acid, in the treatment of established NASH suggest pathways involving cholesterol/bile acid production and clearance play of pivotal role in the pathogenesis of the disease. However, as FXR agonists inhibit the major pathway by which the liver excretes excess cholesterol (conversion to bile acids and biliary excretion), adverse effects upon plasma cholesterol are observed.

Increased hepatocellular cholesterol concentrations can also lead to cholesterol crystal accumulation and cell-death with resultant foam cell formation. Increased oxidized cholesterol (plasma derived or formed in situ) can also incite a hepatic inflammatory reaction and the development of NASH.

Treatments aimed at reducing hepatic cholesterol levels are an attractive target in the prevention and treatment of NASH by both limiting the substrate for both crystal formation and oxidation, but also by decreasing substrate availability for hepatic bile acid synthesis. The advantage of this upstream approach is in addition to tackling key inflammatory inducing components associated with NASH, beneficial effects should also be seen upon atherogenic plasma lipids that frequently accompany the hepatic disease.

WO2010/008299 discloses that structurally enhanced fatty acids including 2-ethyl-2-((5Z,8Z,11Z,14Z,17Z)-icosa-5,8,11,14,17-pentaenylthio)butanoic acid and its derivatives favorably influences lipid profiles, i.a. by lowering plasma triglycerides, plasma cholesterol, plasma insulinetc. Those results demonstrate that 2-ethyl-2-((5Z,8Z,11Z,14Z,17Z)-icosa-5,8,11,14,17-pentaenylthio)butanoic acid and its derivatives may be useful in prevention or treatment of various conditions.

It has surprisingly been found that 2-ethyl-2-((5Z,8Z,11Z,14Z,17Z)-icosa-5,8,11,14,17-pentaenylthio)butanoic acid and its derivatives are useful for preventing and/or treating non-alcoholic steatohepatitis.

BRIEF SUMMARY OF THE INVENTION

The present disclosure relates to a method of preventing and/or treating non-alcoholic steatohepatitis in a subject in need thereof, comprising administering to the subject a pharmaceutically effective amount of a compound of Formula (II):

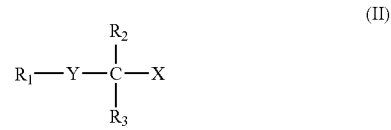

wherein $R_1$ is selected from a $C_{10}$-$C_{22}$ alkenyl having 3-6 double bonds;

$R_2$ and $R_3$ are the same or different and may be selected from a group of substituents consisting of a hydrogen atom, a hydroxy group, an alkyl group, a halogen atom, an alkoxy group, an acyloxy group, an acyl group, an alkenyl group, an alkynyl group, an aryl group, an alkylthio group, an alkoxycarbonyl group, a carboxy group, an alkylsulfinyl group, an alkylsulfonyl group, an amino group, and an alkylamino group, provided that $R_2$ and $R_3$ cannot both be a hydrogen atom; or $R_2$ and $R_3$ can be connected in order to form a cycloalkane like cyclopropane, cyclobutane, cyclopentane or cyclohexane;

Y is selected from sulphur, sulfoxide, and sulfone;

X is a carboxylic acid or a derivative thereof, wherein the derivative is a carboxylic ester, a glyceride, a carboxamide or a phospholipid; or a pharmaceutically acceptable salt, solvate, or solvate of such a salt.

An equal aspect of the disclosure relates to use of a pharmaceutically effective amount of a compound of Formula (II):

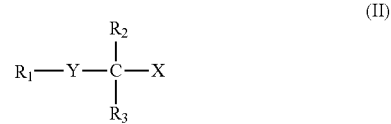

wherein $R_1$; is selected from a $C_{10}$-$C_{22}$ alkenyl having 3-6 double bonds;

$R_2$ and $R_3$ are the same or different and may be selected from a group of substituents consisting of a hydrogen atom, a hydroxy group, an alkyl group, a halogen atom, an alkoxy group, an acyloxy group, an acyl group, an alkenyl group, an alkynyl group, an aryl group, an alkylthio group, an alkoxycarbonyl group, a carboxy group, an alkylsulfinyl group, an alkylsulfonyl group, an amino group, and an alkylamino group, provided that $R_2$ and $R_3$ cannot both be a hydrogen atom; or $R_2$ and $R_3$ can be connected in order to form a cycloalkane like cyclopropane, cyclobutane, cyclopentane or cyclohexane;

Y is selected from sulphur, sulfoxide, and sulfone;

X is a carboxylic acid or a derivative thereof, wherein the derivative is a carboxylic ester, a glyceride, a carboxamide, or a phospholipid; or a pharmaceutically acceptable salt, solvate, or solvate of such a salt, in the manufacture of a medicament for preventing and/or treating non-alcoholic steatohepatitis in a subject in need thereof.

An equal aspect of the disclosure relates to a compound of Formula (II)

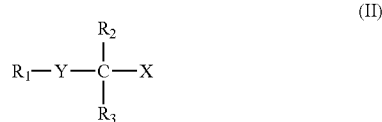

(II)

wherein $R_1$ is selected from a $C_{10}$-$C_{22}$ alkenyl having 3-6 double bonds;

$R_2$ and $R_3$ are the same or different and may be selected from a group of substituents consisting of a hydrogen atom, a hydroxy group, an alkyl group, a halogen atom, an alkoxy group, an acyloxy group, an acyl group, an alkenyl group, an alkynyl group, an aryl group, an alkylthio group, an alkoxycarbonyl group, a carboxy group, an alkylsulfinyl group, an alkylsulfonyl group, an amino group, and an alkylamino group, provided that $R_2$ and $R_3$ cannot both be a hydrogen atom; or $R_2$ and $R_3$ can be connected in order to form a cycloalkane like cyclopropane, cyclobutane, cyclopentane or cyclohexane;

Y is selected from sulphur, sulfoxide, and sulfone;

X represents a carboxylic acid or a derivative thereof, wherein the derivative is a carboxylic ester, a glyceride, a carboxamide, or a phospholipid; or a pharmaceutically acceptable salt, solvate, or solvate of such a salt, for theraputic and/or prophylactic treatment of non-alcoholic steatohepatitis.

In at least one embodiment, $R_2$ and $R_3$ are the same or different and may be selected from a group of substituents consisting of a hydrogen atom, an alkyl group, an alkoxy group, an alkenyl group; or $R_2$ and $R_3$ can be connected in order to form a cycloalkane like cyclopropane, cyclobutane, cyclopentane or cyclohexane; Y is selected from sulphur; X represents a carboxylic acid or a derivative thereof, wherein the derivative is a carboxylic ester, a glyceride or a phospholipid; or a pharmaceutically acceptable salt, solvate, or solvate of such a salt.

More particularly, in one aspect the present disclosure relates to a method of preventing and/or treating non-alcoholic steatohepatitis in a subject in need thereof, comprising administering to the subject a pharmaceutically effective amount of a compound of Formula (I):

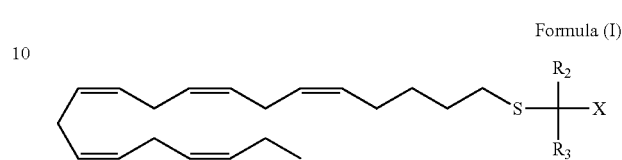

Formula (I)

wherein $R_2$ and $R_3$ and X are defined as for Formula (II) and preferably wherein $R_2$ and $R_3$ are independently chosen from the group of a hydrogen atom and linear, branched, and/or cyclic $C_1$-$C_6$ alkyl groups, with the proviso that $R_2$ and $R_3$ are not both hydrogen; and X is a carboxylic acid or a derivative thereof, wherein the derivative is a carboxylic ester, a glyceride, or a phospholipid; or a pharmaceutically acceptable salt, solvate, or solvate of such a salt.

Likewise, in another aspect the present disclosure relates to use of a pharmaceutically effective amount of a compound of Formula (I):

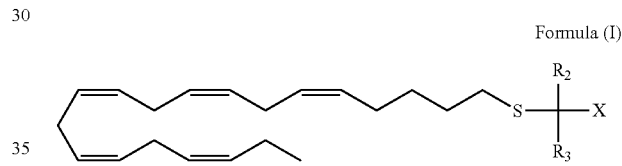

Formula (I)

wherein $R_2$ and $R_3$ and X are defined as for Formula (II) and preferably wherein $R_2$ and $R_3$ are independently chosen from the group of a hydrogen atom and linear, branched, and/or cyclic $C_1$-$C_6$ alkyl groups, with the proviso that $R_2$ and $R_3$ are not both hydrogen; and X is a carboxylic acid or a derivative thereof, wherein the derivative is a carboxylic ester, a glyceride or a phospholipid; or a pharmaceutically acceptable salt, solvate, or solvate of such salt thereof, in the manufacture of a medicament for preventing and/or treating non-alcoholic steatohepatitis in a subject in need thereof.

Likewise, in another aspect the present disclosure relates to a compound of Formula (I):

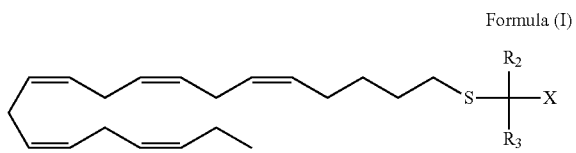

Formula (I)

wherein $R_2$ and $R_3$ and X are defined as for Formula (II) and preferably wherein $R_2$ and $R_3$ are independently chosen from the group of a hydrogen atom and linear, branched, and/or cyclic $C_1$-$C_6$ alkyl groups, with the proviso that $R_2$ and $R_3$ are not both hydrogen; X is a carboxylic acid or a derivative thereof, wherein the derivative is a carboxylic ester, a glyceride or a phospholipid; or a pharmaceutically acceptable salt, solvate, or solvate of such a salt, for preventing and/or treating non-alcoholic steatohepatitis.

For Formula (I), when X is a glyceride, this may be chosen from the group of a triglyceride, a 1,2-diglyceride, a 1,3-diglyceride, a 1-monoglyceride and a 2-monoglyceride.

The present disclosure also includes a method of treating and/or preventing non-alcoholic steatohepatitis in a subject in need thereof, the method comprising administering to the subject a pharmaceutically effective amount of 2-ethyl-2-((5Z,8Z,11Z,14Z,17Z)-icosa-5,8,11,14,17-pentaenylthio) butanoic acid:

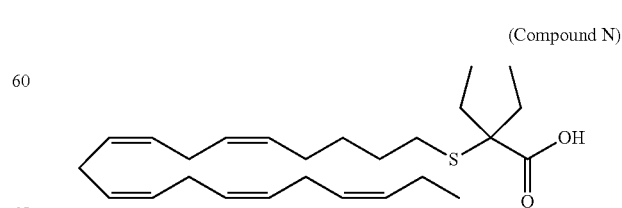

(Compound N)

or a pharmaceutically acceptable salt or ester thereof.

Likewise, the present disclosure also includes use of a pharmaceutically effective amount of 2-ethyl-2-((5Z,8Z,11Z,14Z,17Z)-icosa-5,8,11,14,17-pentaenylthio)butanoic acid (compound N) or a pharmaceutically acceptable salt or ester thereof in the manufacture of a medicament for treating and/or preventing non-alcoholic steatohepatitis in a subject in need thereof.

The present disclosure also relates to 2-ethyl-2-((5Z,8Z,11Z,14Z,17Z)-icosa-5,8,11,14,17-pentaenylthio)butanoic acid (Compound N) or a pharmaceutically acceptable salt or ester thereof, for preventing and/or treating non-alcoholic steatohepatitis.

DETAILED DESCRIPTION

Figure 1:
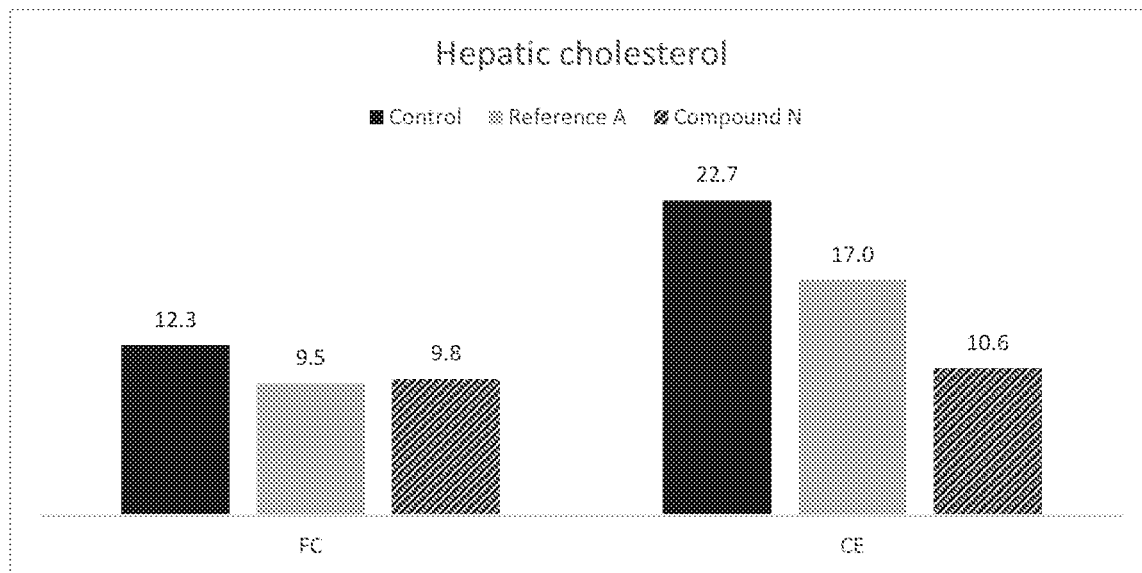
FIG. 1 discloses the effects of Compound N on hepatic cholesterol.

It should be noted that embodiments and features described in the context of one aspect of the present disclosure also apply to the other aspects of the invention. Particularly, the embodiments applying to the method of preventing and/or treating non-alcoholic steatohepatitis according to the present disclosure also apply to the use of a pharmaceutical effective amount of a compound in the manufacture of a medicament for preventing and/or treating non-alcoholic steatohepatitis and likewise to the aspect of a compound for preventing and/or treating non-alcoholic steatohepatitis, all according to the present disclosure.

Particular aspects of the disclosure are described in greater detail below. The terms and definitions as used in the present application and as clarified herein are intended to represent the meaning within the present disclosure.

The singular forms "a," "an," and "the" include plural reference unless the context dictates otherwise.

The terms "approximately" and "about" mean to be nearly the same as a referenced number or value. As used herein, the terms "approximately" and "about" should be generally understood to encompass ±5% of a specified amount, frequency, or value.

The terms "treat" "treating," and "treatment" include any therapeutic application that can benefit a human or non-human mammal. Both human and veterinary treatments are within the scope of the present disclosure. Treatment may be responsive to an existing condition or it may be prophylactic, i.e., preventative.

The terms "administer," "administration," and "administering" as used herein refer to (1) providing, giving, dosing and/or prescribing by either a health practitioner or his authorized agent or under his direction a compound or composition according to the present disclosure, and (2) putting into, taking or consuming by the human patient or person himself or herself, or non-human mammal a compound or composition according to the present disclosure. The terms "preventing and/or treating" and "therapeutic and/or prophylactic treatment of" may interchangeably be used. Typically the compounds of Formula (I) will be used for treating, i.e. therapeutic treatment of, NASH. However, it is also foreseen that in some cases the compound of Formula (I) will be used for preventing or for prophylactic treatment of NASH, for example in cases where a patient have a family history of developing NASH.

The term "pharmaceutically effective amount" means an amount sufficient to achieve the desired pharmacological and/or therapeutic effects, i.e., an amount of the disclosed compound that is effective for its intended purpose. While individual subject/patient needs may vary, the determination of optimal ranges for effective amounts of the disclosed compound is within the skill of the art. Generally, the dosage regimen for treating a disease and/or condition with the compounds presently disclosed may be determined according to a variety of factors such as the type, age, weight, sex, diet, and/or medical condition of the subject/patient.

The term "pharmaceutical composition" means a compound according to the present disclosure in any form suitable for medical use.

The compounds of Formula (I) and (II) may exist in various stereoisomeric forms, including enantiomers, diastereomers, or mixtures thereof. It will be understood that the invention encompasses all optical isomers of the compounds of Formula (I) and (II) as well as mixtures thereof. Hence, compounds of Formula (I) and (II) that exist as diastereomers, racemates, and/or enantiomers are within the scope of the present disclosure.

The present disclosure relates to a method of preventing and/or treating non-alcoholic steatohepatitis in a subject in need thereof, comprising administering to the subject a pharmaceutically effective amount of a compound of Formula (I):

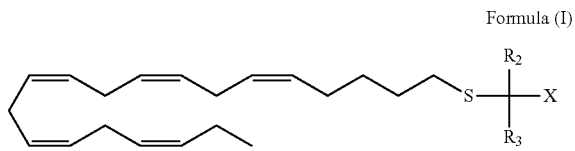

Formula (I)

wherein $R_2$ and $R_3$ are independently chosen from the group of a hydrogen atom and linear, branched, and/or cyclic $C_1$-$C_6$ alkyl groups, with the proviso that $R_2$ and $R_3$ are not both hydrogen; X represents a carboxylic acid or a carboxylic ester; or a pharmaceutically acceptable salt, solvate, solvate of such a salt.

In at least one aspect, the present disclosure relates to use of a pharmaceutically effective amount of a compound of Formula (I):

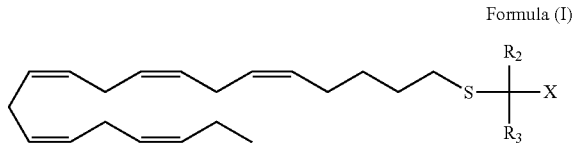

Formula (I)

wherein $R_2$ and $R_3$ are independently chosen from the group of a hydrogen atom and linear, branched, and/or cyclic $C_1$-$C_6$ alkyl groups, with the proviso that $R_2$ and $R_3$ are not both hydrogen; X represents a carboxylic acid or a carboxylic ester; or a pharmaceutically acceptable salt, solvate, solvate of such a salt, for preventing and/or treating non-alcoholic steatohepatitis in a subject in need thereof.

In at least one aspect, the present disclosure relates to a compound of Formula (I):

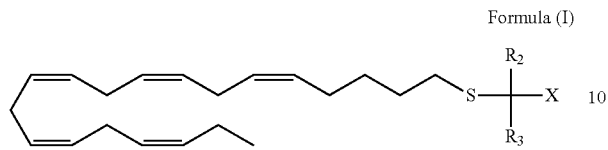

Formula (I)

wherein $R_2$ and $R_3$ are independently chosen from the group of a hydrogen atom and linear, branched, and/or cyclic $C_1$-$C_6$ alkyl groups, with the proviso that $R_2$ and $R_3$ are not both hydrogen; X is a carboxylic acid or a carboxylic ester; or a pharmaceutically acceptable salt, solvate, or solvate of such a salt, for preventing and/or treating non-alcoholic steatohepatitis.

For the compounds of Formula (I), the use of these, and for the method of administering these, the following items of disclosure are included:

In those cases were $R_2$ and $R_3$ are different, the compounds of Formula (I) are capable of existing in stereoisomeric forms. It will be understood that the invention encompasses all optical isomers of the compounds of Formula (I) and mixtures thereof.

In at least one embodiment, $R_2$ and $R_3$ are independently chosen from a hydrogen atom, a methyl group, an ethyl group, a n-propyl group, and an isopropyl group.

In at least one embodiment, $R_2$ and $R_3$ are chosen from a hydrogen atom, a methyl group, and an ethyl group.

In at least one embodiment, one of $R_2$ and $R_3$ is a hydrogen atom and the other one of $R_2$ and $R_3$ is chosen from a $C_1$-$C_3$ alkyl group. In one embodiment, one of $R_2$ and $R_3$ is a hydrogen atom and the other one of $R_2$ and $R_3$ is chosen from a methyl group or an ethyl group.

In at least one embodiment $R_2$ and $R_3$ are independently $C_1$-$C_6$ alkyl groups. In one embodiment both $R_2$ and $R_3$ are $C_1$-$C_3$ alkyl groups. In one embodiment $R_2$ and $R_3$ are the same or different and each are independently chosen from a methyl group, an ethyl group, an n-propyl group, or an isopropyl group. In one embodiment $R_2$ and R3 are the same and are selected from a pair of methyl groups, a pair of ethyl groups, a pair of n-propyl groups and a pair of isopropyl groups. In at least one preferred embodiment R2 and R3 are ethyl groups. In one embodiment, one of R2 and R3 is a methyl group and the other one is an ethyl group. In one embodiment, one of R2 and R3 is an ethyl group and the other one is a n-propyl group.

In at least one embodiment, X is a carboxylic acid. In one embodiment, wherein X is a carboxylic ester, this is a C1-C6 alkyl ester. This may be chosen from a methyl ester, an ethyl ester, an isopropyl ester, a n-butyl ester and a tert-butyl ester. Preferably, the ester is selected from a methyl ester and an ethyl ester.

In at least one embodiment, the compound may be present in its various stereoisomeric forms, such as an enantiomer (R or S), diastereomer, or mixtures thereof.

In at least one embodiment, the compound is present in racemic form. In one embodiment, the compound is present in its R form. In another embodiment, the compound is present in its S form.

In cases, where the compound according to Formula (I) is a salt of a counter-ion with at east one stereogenic center, or ester of an alcohol with at least one stereogenic center, the compound may have multiple stereocenters. In those situations, the compounds of the present disclosure may exist as diastereomers. Thus, in at least one embodiment, the compounds of the present disclosure are present as at least one diastereomer.

In at least one embodiment, the compound of the present disclosure is 2-ethyl-2-((5Z,8Z,11Z,14Z,17Z)-icosa-5,8,11,14,17-pentaenylthio)butanoic acid:

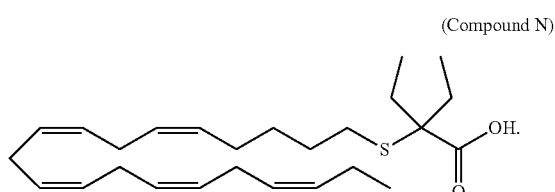

(Compound N)

Given the established adverse effects upon hepatic cholesterol upon NASH from both animal studies and human tissue samples, the described examples clearly suggest that compounds of Formula (I) such as Compound N may have beneficial effects in the prevention and/or treatment of NASH.

It was previously shown that both Compound N and Reference A (2-((5Z,8Z,11Z,14Z,17Z)-icosa-5,8,11,14,17-pentaenyloxy)butanoic acid prepared according to Example 2 of WO2010/128401) could significantly decrease plasma cholesterol in APOE*3Leiden.CETP double transgenic mice. The absolute reductions achieved by both compounds were comparable and the proposed mechanism's by which these reductions are achieved appear similar (SREPB-2 activation and increased hepatic LDL-R expression). It was therefore surprising to find the clear differences observed between the compounds in a number of key components of NASH as described in the examples. These differences may be related to varying effects upon hepatic cholesterol biosynthesis as the differences in hepatic cholesterol ester levels cannot be explained by increased hepatic cholesterol uptake (rate of uptake same for both compounds, data not shown).

Although only fecal bile acid content was measured in this model, the reduction in bile acid excretion along with the decreased hepatic cholesterol ester content suggest that less cellular cholesterol may be available for bile acid synthesis. As evidenced by the beneficial effects of FXR agonists (although there are additional mechanisms by which these compounds work), a reduction in bile acid synthesis should have both anti-inflammatory and anti-fibrotic effects in human NASH. A reduced availability of hepatic cholesterol should also reduce cholesterol crystal formation and oxidised cholesterol content, both potentially important mediators of NASH in humans. The significantly reduced plasma residence time of cholesterol demonstrated in earlier studies (data not shown) may also reduce oxidised cholesterol uptake.

Although reducing hepatic cholesterol has anti-inflammatory effects in animal models of NASH, whether the difference in hepatic cholesterol can explain the superior effects of Compound N versus Reference A upon hepatic inflammation (as shown in examples) is uncertain. The mechanism by which Compound N, and not Reference A, reduces macrovesicular steatosis is also uncertain, but does not appear to be mediated by increased beta-oxidation of fatty acids (data not shown).

As previously described, multiple independent and interdependent metabolic, inflammatory and ultimately fibrotic components converge in the development of human NASH. It is likely that any successful treatment will need to address all aspects of NASH, preferably via upstream metabolic/inflammatory targets. The unique, broad spectrum of metabolic, inflammatory and histological effects as described in the enclosed examples provide justification for the testing of the efficacy of Compound N in human subjects with NASH.

Compounds of Formula (I) can be prepared as described, for example, in PCT Application WO 2010/008299 filed Jul. 13, 2009, and according to Examples below.

Examples 1-13 are exemplary and one skilled in the art would understand how to apply these general methods to arrive at other compounds within the scope of Formula (I). Compounds of the present disclosure may be in the form of a pharmaceutically acceptable salt or ester. For example, the compounds of Formula (I) may be in the form of esters, such as a phospholipid, a glyceride or a $C_1$-$C_6$-alkyl ester. In at least one embodiment, the ester is chosen from a glyceride or a $C_1$-$C_6$-alkyl ester. In at least one embodiment, the ester is chosen from a triglyceride, a 1,2-diglyceride, a 1,3-diglyceride, a 1-monoglyceride, a 2-monoglyceride, a methyl ester, an ethyl ester, a propyl ester, a isopropyl ester, a n-butyl ester and a tert-butyl ester. In at least one embodiment, the compound of Formula (I) is present as a methyl ester, an ethyl ester, an isopropyl ester, a n-butyl ester or a tert-butyl ester, for example as a methyl ester or an ethyl ester. Typically, esters represented by Formula (I) (e.g., ethyl esters) will be hydrolyzed in the gastrointestinal tract.

Salts suitable for the present disclosure include, but are not limited to, salts of $NH^{4+}$; metal ions such as $Li^+$, $Na^+$, $K^+$, $Mg^{2+}$, or $Ca^{2+}$; a protonated primary amine such as tert-butyl ammonium, (3S,5S,7S)-adamantan-1-ammonium, 1,3-dihydroxy-2-(hydroxymethyl)propan-2-ammonium, a protonated aminopyridine (e.g., pyridine-2-ammonium); a protonated secondary amine such as diethylammonium, 2,3,4,5,6-pentahydroxy-N-methylhexan-1-ammonium, N-ethylnaphthalen-1-ammonium, a protonated tertiary amine such as 4-methylmorpholin-4-ium, a protonated quaternary amine such as 2-hydroxy-N,N,N-trimethylethan-1-aminium and a protonated guanidine such as amino((4-amino-4-carboxybutyl)amino)methaniminium or a protonated heterocycle such as 1H-imidazol-3-ium. Additional examples of suitable salts include salts of a diprotonated diamine such as ethane-1,2-diammonium or piperazine-1,4-diium. Other salts according to the present disclosure may comprise protonated Chitosan:

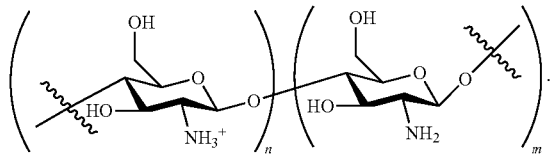

In at least embodiment, the salts are chosen from a sodium salt, a calcium salt, and a choline salt. In one embodiment the salt is a sodium salt or a calcium salt.

The present disclosure provides for a method of preventing or treating NASH in a subject in need thereof, comprising administering to the subject a pharmaceutically effective amount of a compound of Formula (I). The subject may be a human or a non-human mammal. The compounds presently disclosed may be administered as a medicament, such as in a pharmaceutical composition. Hence, another aspect of the invention is a composition, such as a pharmaceutical composition, comprising a compound of Formula (I) for preventing and/or treating non-alcoholic steatohepatitis.

The composition presently disclosed may comprise at least one compound of Formula (I) and optionally at least one non-active pharmaceutical ingredient, i.e., excipient. Non-active ingredients may solubilize, suspend, thicken, dilute, emulsify, stabilize, preserve, protect, color, flavor, and/or fashion active ingredients into an applicable and efficacious preparation, such that it may be safe, convenient, and/or otherwise acceptable for use. Examples of excipients include, but are not limited to, solvents, carriers, diluents, binders, fillers, sweeteners, aromas, pH modifiers, viscosity modifiers, antioxidants, extenders, humectants, disintegrating agents, solution-retarding agents, absorption accelerators, wetting agents, absorbents, lubricants, coloring agents, dispersing agents, and preservatives. Excipients may have more than one role or function, or may be classified in more than one group; classifications are descriptive only and are not intended to be limiting. In some embodiments, for example, the at least one excipient may be chosen from corn starch, lactose, glucose, microcrystalline cellulose, magnesium stearate, polyvinylpyrrolidone, citric acid, tartaric acid, water, ethanol, glycerol, sorbitol, polyethylene glycol, propylene glycol, cetylstearyl alcohol, carboxymethylcellulose, and fatty substances such as hard fat or suitable mixtures thereof. In some embodiments, the compositions presently disclosed comprise at least one compound of Formula (I) and at least one pharmaceutically acceptable antioxidant, e.g., tocopherol such as alpha-tocopherol, beta-tocopherol, gamma-tocopherol, and delta-tocopherol, or mixtures thereof, BHA such as 2-tert-butyl-4-hydroxyanisole and 3-tert-butyl-4-hydroxyanisole, or mixtures thereof and BHT (3,5-di-tert-butyl-4-hydroxytoluene), or mixtures thereof.

The compositions presently disclosed may be formulated in oral administration forms, e.g., tablets or gelatin soft or hard capsules. The dosage form can be of any shape suitable for oral administration, such as spherical, oval, ellipsoidal, cube-shaped, regular, and/or irregular shaped. Conventional formulation techniques known in the art may be used to formulate the compounds according to the present disclosure. In some embodiments, the composition may be in the form of a gelatin capsule or a tablet.

A suitable daily dosage of a compound of Formula (I) may range from about 5 mg to about 2 g. For example, in some embodiments, the daily dose ranges from about 10 mg to about 1.5 g, from about 50 mg to about 1 g, from about 100 mg to about 1 g, from about 150 mg to about 900 mg, from about 50 mg to about 800 mg, from about 100 mg to about 800 mg, from about 100 mg to about 600 mg, from about 150 to about 550 mg, or from about 200 to about 500 mg. In at least one embodiment, the daily dose ranges from about 200 mg to about 600 mg. In at least one embodiment, the daily dose is about 50 mg, about 100 mg, about 200 mg, about 300 mg, about 400 mg, about 500 mg, about 600 mg, about 700 mg, about 800 mg, or about 900 mg. The compound(s) may be administered, for example, once, twice, or three times per day. In at least one embodiment, the compound of Formula (I) is administered in an amount ranging from about 200 mg to about 800 mg per dose. In at least one embodiment, the compound of Formula (I) is administered once per day.

The present inventors have found that compounds of Formula (I), such as 2-ethyl-2-((5Z,8Z,11Z,14Z,17Z)-icosa-5,8,11,14,17-pentaenylthio)butanoic acid, have remarkably good pharmaceutical activity. Surprisingly, the compounds of Formula (I) presently disclosed exhibit improved biological activity compared to naturally occurring omega-3 fatty acids, such as EPA and DHA for preventing and/or treating NASH.

Some specific embodiments of the invention is listed below:

A method of preventing and/or treating non-alcoholic steatohepatitis in a subject in need thereof, comprising administering to the subject a pharmaceutically effective amount of a compound of Formula (I):

Formula (I)

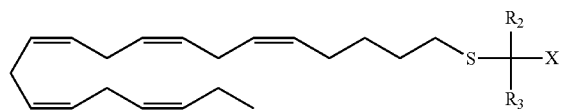

wherein $R_2$ and $R_3$ are independently selected from the group of a hydrogen atom and linear, branched, and/or cyclic $C_1$-$C_6$ alkyl groups, with the proviso that $R_2$ and $R_3$ are not both hydrogen; X is a carboxylic acid or a derivative thereof, wherein the derivative is a carboxylic ester, a glyceride, or a phospholipid; or a pharmaceutically acceptable salt, solvate, or solvate of such a salt. More specifically $R_2$ and $R_3$ are independently chosen from a hydrogen atom, a methyl group, an ethyl group, a n-propyl group, and an isopropyl group. More specifically $R_2$ and $R_3$ are independently $C_1$-$C_6$ alkyl groups, such as $R_2$ and $R_3$ are the same or different and each are independently chosen from a methyl group, an ethyl group, an n-propyl group, or an isopropyl group. Preferably $R_2$ and $R_3$ are both ethyl groups. In one embodiment X is a carboxylic acid. In another embodiment, X is a carboxylic ester, such as a $C_1$-$C_6$ alkyl ester, such as chosen from a methyl ester, an ethyl ester, an isopropyl ester, a n-butyl ester, and a tert-butyl ester, such as chosen from methyl ester and an ethyl ester. The method above, wherein the glyceride is chosen from a triglyceride, a 1,2-diglyceride, a 1,3-diglyceride, a 1-monoglyceride, and 2-monoglyceride. In one embodiment the compound is present in the form of an enantiomer, diastereomer, or mixture thereof. The method above wherein the compound is present in its R form. In one embodiment the compound is present in its S form. In another embodiment, the compound is present in racemic form. In a preferred embodiment, the invention provides a method as above, wherein $R_2$ and $R_3$ are ethyl groups and X is a carboxylic acid. The pharmaceutically effective amount of the compound of Formula (I) ranges from about 5 mg to about 2 g per dose, such as from about 200 mg to about 800 mg per dose, such as about 600 mg. In one embodiment of the method the subject is a human. The compound is preferably administered daily, such as once daily. The method as disclosed wherein the compound is formulated as a pharmaceutical composition for oral administration, such as in the form of a gelatin capsule or a tablet. The pharmaceutical composition may further comprise at least one binder, excipient, diluent, or any combinations thereof. The pharmaceutical composition further comprises an antioxidant, such as chosen from tocopherol, BHA, and BHT, or a mixture thereof. A method of treating and/or preventing non-alcoholic steatohepatitis in a subject in need thereof, the method comprising administering to the subject a pharmaceutically effective amount of 2-ethyl-2-((5Z,8Z,11Z,14Z,17Z)-icosa-5,8,11,14,17-pentaenylthio)butanoic acid:

(Compound N)

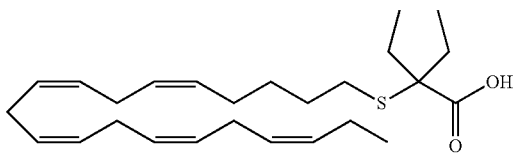 [SMILES: CC/C=C\C/C=C\C/C=C\C/C=C\C/C=C\CCCCSC(CC)(CC)C(=O)O]

or a pharmaceutically acceptable salt or ester thereof.

Use of a pharmaceutically effective amount of a compound of Formula (I)

Formula (I)

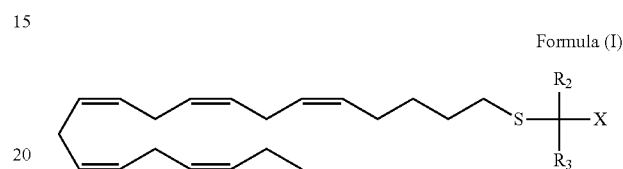

wherein $R_2$ and $R_3$ are independently selected from the group of a hydrogen atom and linear, branched, and/or cyclic $C_1$-$C_6$ alkyl groups, with the proviso that $R_2$ and $R_3$ are not both hydrogen; X is a carboxylic acid or a derivative thereof, wherein the derivative is a carboxylic ester, a glyceride or a phospholipid; or a pharmaceutically acceptable salt, solvate, or solvate of such a salt, in the manufacture of a medicament for preventing and/or treating non-alcoholic steatohepatitis in a subject in need thereof. Use of a pharmaceutically effective amount of 2-ethyl-2-((5Z,8Z,11Z,14Z,17Z)-icosa-5,8,11,14,17-pentaenylthio)butanoic acid:

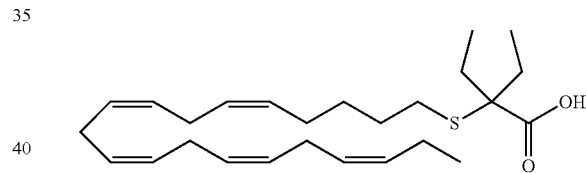

or a pharmaceutically acceptable salt or ester thereof in the manufacture of a medicament for treating and/or preventing non-alcoholic steatohepatitis in a subject in need thereof.

The use above, wherein the pharmaceutically-effective amount ranges from about 200 mg to about 800 mg per dose. The use above wherein 2-ethyl-2-((5Z,8Z,11Z,14Z,17Z)-icosa-5,8,11,14,17-pentaenylthio)butanoic acid is administered once daily.

EXAMPLES

The present disclosure may be further described by the following non-limiting examples, in which standard techniques known to the skilled chemist and techniques analogous to those described in these examples may be used where appropriate. It is understood that the skilled artisan will envision additional embodiments consistent with the disclosure provided herein.

Unless otherwise stated, reactions were carried out at room temperature, typically in the range between 18-25° C. with solvents of HPLC grade under anhydrous conditions. Evaporations were carried out by rotary evaporation in vacuo. Column chromatography was performed by the flash procedure on silica gel 40-63 μm (Merck) or by an Armen Spotflash using the pre-packed silica gel columns "Mini- VarioFlash", "SuperVarioFlash", "SuperVarioPrep" or "EasyVarioPrep" (Merck). Nuclear magnetic resonance (NMR) shift values were recorded on a Bruker Avance DPX 200 or 300 instrument with peak multiplicities described as follows: s, singlet; d, doublet; dd, double doublet; t, triplet; q, quartet; p, pentet; m, multiplett; br, broad. The mass spectra were recorded with a LC/MS spectrometer. Separation was performed using a Agilent 1100 series module on a Eclipse XDB-018 2.1×150 mm column with gradient elution. As eluent were used a gradient of 5-95% acetonitrile in buffers containing 0.01% trifluoroacetic acid or 0.005% sodium formate. The mass spectra were recorded with a Gl956A mass spectrometer (electrospray, 3000 V) switching positive and negative ionization mode. Reported yields are illustrative and do not necessarily represent the maximum yield attainable.

PREPARATION OF INTERMEDIATES

Example 1: Preparation of S-(5Z,8Z,11Z,14Z,17Z)-icosa-5,8,11,14,17-pentaenyl ethanethioate

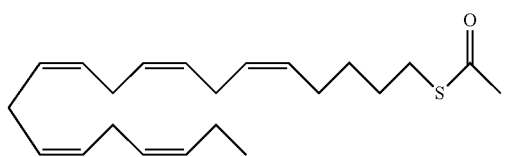 [SMILES: CC/C=C\C/C=C\C/C=C\C/C=C\C/C=C\CCCCSC(C)=O]

Triphenylphosphine (21.0 g, 80 mmol) was dissolved in dry THF (170 mL) at 0° C. under inert atmosphere and added DIAD (15.8 mL, 80 mmol) dropwise. After 40 minutes at 0° C. the white suspension was added dropwise to a solution of (5Z,8Z,11Z,14Z,17Z)-icosa-5,8,11,14,17-pentaen-1-ol (11.5 g, 40 mmol) and thioacetic acid (5.7 mL, 80 mmol) in dry THF (50 mL) during 15 minutes. The resulting turbid mixture was stirred at 0° C. for 30 minutes, followed by ambient temperature for 1.5 hour. Heptane was added (200 mL), the mixture was stirred for ten minutes and the precipitated white solid removed by filtration and rinsed with heptane (150 mL). The residue was concentrated to remove most of the THF and stirred at ambient for 18 hours. The mixture was filtered, concentrated and added heptane (200 mL). The resulting mixture was stirred for 2 hours, filtered and evaporated. The residue was purified by flash chromatography on silica gel, using EtOAc:Heptane (2:98), followed by EtOAc:Heptane (4:96) and finally EtOAc:Heptane (5:95). Concentration of the appropriate fractions provided 11.0 g (79% yield) of the title compound as oil. 1H-NMR (300 MHz, CDCl3): δ 0.95 (t, 3H, J=7.5 Hz), 1.40 (m, 2H), 1.58 (m, 2H), 2.06 (m, 4H), 2.29 (s, 3H), 2.77-2.87 (m, 10H), 5.25-5.42 (m, 10H); MS (Cl(CH4): 347 [M+C3H5]+375 [M+C2H5]+, 347 [M+H]+, 333 [M−CH2]+, 305 [R−SH]+.

Example 2: Preparation of (5Z,8Z,11Z,14Z,17Z)-icosa-5,8,11,14,17-pentaene-1-thiol

S-(5Z,8Z,11Z,14Z,17Z)-Icosa-5,8,11,14,17-pentaenyl ethanethioate (7.00 g, 20.2 mmol) was dissolved in MeOH (100 mL) by stirring 10 minutes until the droplets of oil dissolved, before anhydrous potassium carbonate, K2CO3 (2.79 g, 20.2 mmol) was added in one portion. The mixture was stirred for 1 hour and 20 minutes at ambient temperature and quenched by addition of 1 M HCl (50 mL) and water (150 mL). The white cloudy mixture was added Et2O (250 mL) and the phases were separated. The water phase was extracted with Et2O (2×250 mL). The combined organic phases were washed with brine (250 mL) and dried (MgSO4). Filtration and evaporation gave the title compound as oil (5.99 g, 97% yield), which was used without further purification. 1H-NMR (300 MHz, CDCl3): δ 0.96 (t, 3H, J=7.5 Hz), 1.31 (t, 1H, J=7.8 Hz), 1.44 (m, 2H), 1.61 (m, 2H), 2.06 (m, 4H), 2.51 (m, 2H), 2.77-2.85 (m, 8H), 5.28-5.41 (m, 10H); MS (Cl(CH4)): 345 [M+C3H5]+, 333 [M+C2H5]+, 305 [M+H]+, 271 [M−SH]+.

Example 3: Preparation of (5Z,8Z,11Z,14Z,17Z)-icosa-5,8,11,14,17-pentaenyl methanesulfonate

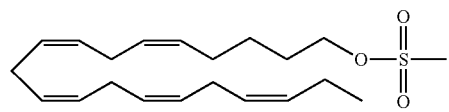 [SMILES: CC/C=C\C/C=C\C/C=C\C/C=C\C/C=C\CCCCOS(C)(=O)=O]

Et3N (1.50 mL, 10.8 mmol) and methanesulfonyl chloride (402 µL, 5.20 mmol) was added to a solution of (5Z,8Z,11Z,14Z,17Z)-icosa-5,8,11,14,17-pentaen-1-ol (1.15 g, 4.0 mmol) in CH2Cl2 (40 mL) held at 0° C. under nitrogen. The mixture was stirred at 0° C. for one hour, and poured into ice-water (100 g) and the water phase extracted with Et2O (50 mL). The combined organic extracts were added 0.5 M H2SO4 (35 mL), the organic phase washed with NaHCO3 (sat. aq.) (25 mL), before dried (Mg2SO4, 10 gram). Filtration and concentration in vacua afforded 1.24 gram of crude oil. Purification on Armen, SVP D26 column packed with 30 gram of 15-40 µm Merck silica, flow 20 mL/min, UV 210 nm and collecting 15 mL fraction, was performed using gradient elution: (starting heptane:EtOAc (100:0) and increasing during 10 min. to 10% EtOAc, then increasing 5 min. to 20% EtOAc (hold 10 min.), then increasing in 5 min. to 40% EtOAc (hold 0 min.). Fractions 6-14 afforded 1.16 g (79% yield) of the title compound as oil. 1H-NMR (300 MHz, CDCl3): δ 0.97 (t, 3H), 1.50 (m, 2H), 1.75 (m, 2H), 2.03-2.15 (m, 4H), 2.76-2.86 (m, 8H), 2.99 (s, 3H), 4.22 (t, 2H), 5.27-5.40 (m, 10H); MS (electrospray): 389.2 [M+Na]+.

Example 4: Preparation of (4S,5R)-3-((S)-2-((5Z,8Z,11Z,14Z,17Z)-icosa-5,8,11,14,17-pentaenylthio)butanoyl)-4-methyl-5-phenyloxazolidin-2-one and (4S,5R)-3-((R)-2-((5Z,8Z,11Z,14Z,17Z)-icosa-5,8,11,14,17-pentaenylthio)butanoyl)-4-methyl-5-phenyloxazolidin-2-one

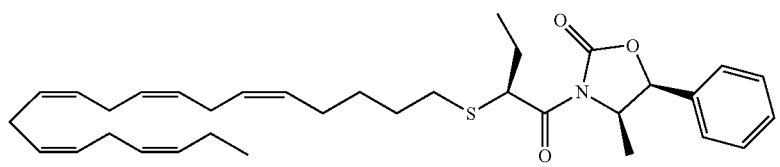

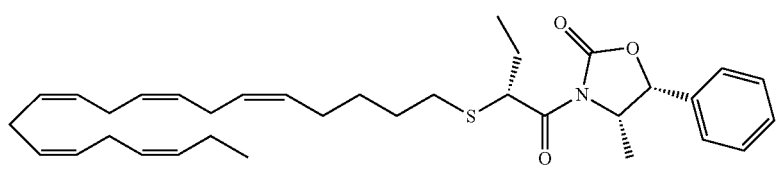

A mixture of 2-((5Z,8Z,11Z,14Z,17Z)-icosa-5,8,11,14,17-pentaenylthio)butanoic acid (3.0 g, 7.9 mmol) in dry dichloromethane (40 mL) held at 0° C. under nitrogen was added DMAP (1.0 g, 9.5 mmol) and 1,3-dicyclohexylcarbodiimide (DCC) (1.8 g, 8.7 mmol). The resulting mixture was stirred at 0° C. for 20 minutes, (4S,5R)-4-methyl-5-phenyl-2-oxazolidinone (1.7 g, 9.5 mmol) was added and the resulting turbid mixture was stirred at ambient temperature for 24 hours. The mixture was filtrated and concentrated under reduced pressure to give a crude product containing the desired product as a mixture of two diastereomers. The residue was purified by flash chromatography on Armen Spotflash instrument on silica gel using 2% ethyl acetate in heptane as eluent. The two diastereomers were separated and the appropriate fractions were concentrated. (4S,5R)-3-((R)-2-((5Z,8Z,11Z,14Z,17Z)-Icosa-5,8,11,14,17-pentaenylthio)butanoyl)-4-methyl-5-phenyloxazolidin-2-one eluted first and was obtained in 0.95 g (47% yield) as an oil. 1.47 g (67% yield) of (4S,5R)-3-((S)-2-((5Z,8Z,11Z,14Z,17Z)-icosa-5,8,11,14,17-pentaenylthio)butanoyl)-4-methyl-5-phenyloxazolidin-2-one was obtained as an oil. (4S,5R)-3-((R)-2-((5Z,8Z,11Z,14Z,17Z)-icosa-5,8,11,14,17-pentaenylthio)butanoyl)-4-methyl-5-phenyloxazolidin-2-one (E1):1H-NMR (300 MHz, CDCl3): δ 0.93-1.06 (m, 9H), 1.45-1.60 (m, 4H), 1.75-1.85 (m, 1H), 2.05-2.15 (m, 5H), 2.55-2.70 (m, 2H), 2.87 (m, 8H), 4.69 (t, 1H), 4.79 (p, 1H), 5.30-5.45 (m, 10H), 5.72 (d, 1H), 7.32 (m, 2H), 7.43 (m, 3H). (4S,5R)-3-((S)-2-((5Z,8Z,11Z,14Z,17Z)-icosa-5,8,11,14,17-pentaenylthio)butanoyl)-4-methyl-5-phenyloxazolidin-2-one:1H-NMR (300 MHz, CDCl3): δ 0.93 (d, 3H), 0.99 (t, 3H), 1.05 (t, 3H), 1.40-1.56 (m, 4H), 1.50-1.75 (m, 1H), 2.00-2.15 (m, 5H), 2.47-2.65 (m, 2H), 2.83 (m, 8H), 4.62 (t, 1H), 4.85 (p, 1H), 5.25-5.45 (m, 10H), 5.70 (d, 1H), 7.32 (m, 2H), 7.43 (m, 3H).

PREPARATION OF TARGET MOLECULES

Example 5: Preparation of ethyl 2-((5Z,8Z,11Z,14Z,17Z)-icosa-5,8,11,14,17-pentaenylthio)propanoate

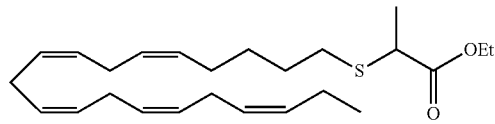 [SMILES: CC/C=C\C/C=C\C/C=C\C/C=C\C/C=C\CCCCSC(C)C(=O)OCC]

(5Z,8Z,11Z,14Z,17Z)-icosa-5,8,11,14,17-pentaene-1-thiol (305 mg, 1.00 mmol) was added to a solution of NaH (60% in mineral oil, 44 mg, 1.10 mmol) in dry DMF (10 mL) held at 0° C. under inert atmosphere. After ten minutes, ethyl bromopropionate (1364, 1.05 mmol) was added and the mixture was stirred for 1.5 hour at 0° C. The reaction mixture was added sat. aq. NH4Cl (20 mL) and heptane (50 mL). The phases were separated and the water phase extracted with heptane (2×25 mL). The combined organics were washed with brine (25 mL), dried (MgSO4), filtered and evaporated to give 376 mg of title compound as crude oil. Purification by flash chromatography on silica gel using gradient elution (starting pure heptane and increasing stepwise to heptane:EtOAc 95:5) afforded 318 mg (79% yield) of the title compound as oil. $^1$H-NMR (300 MHz, CDCl$_3$): δ 0.95 (t, 3H), 1.25 (t, 3H), 1.41 (d, 3H), 1.44 (m, 2H), 1.58 (m, 2H), 2.06 (m, 4H), 2.60 (m, 2H), 2.71-2.85 (m, 8H), 3.36 (d, 1H), 4.17 (m, 2H), 5.25-5.40 (m, 10H); MS (Cl (CH$_4$)): 445 [M+C$_3$H$_5$]$^+$, 433 [M+C$_2$H$_5$]$^+$, 405 [M+H]$^+$, 359 [M−OEt]$^+$, 331 [M−CO$_2$Et]$^+$, 303 [R−S]$^{*+}$.

Example 6: Preparation of ethyl 2-((5Z,8Z,11Z,14Z,17Z)-icosa-5,8,11,14,17-pentaenylthio)butanoate

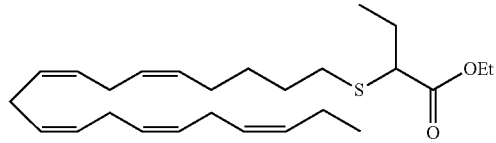 [SMILES: CC/C=C\C/C=C\C/C=C\C/C=C\C/C=C\CCCCSC(CC)C(=O)OCC]

To a solution of (5Z,8Z,11Z,14Z,17Z)-Icosa-5,8,11,14,17-pentaene-1-thio (305 mg, 1.00 mmol) in dry DMF (10 mL) at 0° C. under inert atmosphere was added NaH (60% in mineral oil, 44 mg, 1.1 mmol). After fifteen minutes, ethyl bromobutyrate (154 µL, 1.05 mmol) was added. The mixture was stirred for 1 hour at 0° C. Sat. aq. NH$_4$Cl (20 mL), water (20 mL) and heptane (50 mL) were added. The phases were separated and the water phase was extracted with heptane (2×25 mL). The combined organics were washed with water (25 mL) and brine (25 mL), dried (MgSO$_4$), filtered and evaporated to give 379 mg of the title compound as a crude oil. Purification by flash chromatography on silica gel using gradient elution (starting pure heptane and increasing stepwise to heptane:EtOAc 95:5) afforded 345 mg (82% yield) of the title compound as oil. $^1$H-NMR (300 MHz, CDCl$_3$): δ 0.93-1.00 (m, 6H), 1.25 (t, 3H), 1.44 (m, 2H), 1.59 (m, 2H), 1.68 (m, 1H), 1.87 (m, 1H), 2.07 (m, 4H), 2.57 (m, 2H), 2.73-2.88 (m, 8H), 3.12 (m, 1H), 4.17 (m, 2H), 5.27-5.46 (m, 10H); MS (CI (CH$_4$)): 459 [M+C$_3$H$_5$]$^+$, 447 [M+C$_2$H$_5$]$^+$, 419 [M+H]$^+$, 373 [M–OEt]$^+$, 345 [M–CO$_2$Et]$^+$, 303 [R–S]$^{*+}$.

Example 7: Preparation of 2-1(5Z,8Z,11Z,14Z,17Z)-icosa-5,8,11,14,17-pentaenylthio)butanoic acid

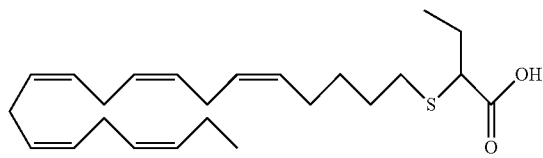 [SMILES: CC/C=C\C/C=C\C/C=C\C/C=C\C/C=C\CCCCSC(CC)C(=O)O]

Ethyl 2-((5Z,8Z,11Z,14Z,17Z)-icosa-5,8,11,14,17-pentaenylthio)butanoate (209 mg, 0.50 mmol) was dissolved in ethanol (2.5 mL) and added to a solution of LiOH×H$_2$O (168 mg, 4.0 mmol) in water (2.5 mL). The resulting turbid solution was stirred at 70° C. under inert atmosphere for 2 hours, cooled and added water (10 mL) and 1 M HCl (5 mL) to pH=1-2. The mixture was extracted with heptane (2×20 mL) and diethyl ether (20 mL). The combined organic extracts were dried (MgSO$_4$), filtered and concentrated under reduced pressure to give 154 mg of the title compound as crude oil. Purification by flash chromatography on silica gel using gradient elution (starting with pure heptane and increasing stepwise to heptane:EtOAc (with 5% HOAc) 80:20) afforded 151 mg (77% yield) of the title compound as oil. $^1$H-NMR (300 MHz, CDCl$_3$): δ 0.95 (t, 3H), 1.02 (t, 3H), 1.46 (m, 2H), 1.52-1.78 (m, 3H), 1.90 (m, 1H), 2.05 (m, 4H), 2.63 (m, 2H), 2.75-2.90 (m, 8H), 3.14 (t, 1H) (m, 1H), 4.17 (m, 2H), 5.27-5.46 (m, 10H).

Example 8: Preparation of (S)-2-(5Z,8Z,11Z,14Z,17Z)-icosa-5,8,11,14,17-pentaenylthio)butanoic acid

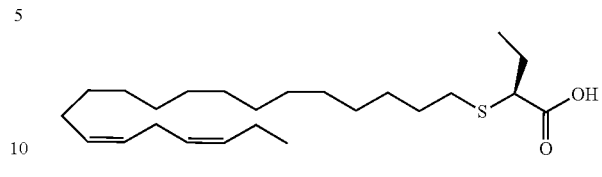

Hydrogen peroxide (30% in water, 0.71 mL, 6.91 mmol) and lithium hydroxide monohydrate (0.15 g, 3.46 mmol) was added to a solution of (4S,5R)-3-((S)-2-((5Z,8Z,11Z,14Z,17Z)-icosa-5,8,11,14,17-pentaenylthio)butanoyl)-4-methyl-5-phenylaxazolidin-2-one (0.95 g, 1.73 mmol) in tetrahydrofuran (12 mL) and water (4 mL) held at 0° C. under nitrogen. The reaction mixture was stirred at 0° C. for 30 minutes. 10% Na$_2$SO$_{3(aq)}$ (30 mL) was added, the pH was adjusted to ~2 with 5M HCl and the mixture was extracted twice with heptane (30 mL). The combined organic extract was dried (Na$_2$SO$_4$), filtered and concentrated. The residue was subjected to flash chromatography on silica gel using increasingly polar mixtures of heptane and ethyl acetate (98:8→1:1) as eluent. Concentration of the appropriate fractions afforded 0.15 g (17% yield) of the title product as an oil. $^1$H-NMR (300 MHz, CDCl$_3$): δ 1.00 (t, 3H), 1.07 (t, 3H), 1.46 (m, 2H), 1.60-1.75 (m, 3H), 1.85 (m, 1H), 2.10 (m, 4H), 2.66 (m, 2H), 2.80-2.90 (m, 8H), 3.21 (t, 1H), 5.35-5.45 (m, 10H); MS (electrospray): 389.3 [M–H]$^-$; [ ]$_D$ –49° (c=0.12, ethanol).

Example 9: Preparation of (R)-2-((5Z,8Z,11Z,14Z,17Z)-icosa-5,8,11,14,17-pentaenylthio)butanoic acid

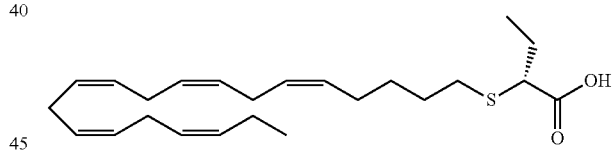

Hydrogen peroxide (30% in water, 1.04 mL, 10.2 mmol) and lithium hydroxide monohydrate (0.21 g, 5.09 mmol) was added to a solution of (4S,5R)-3-((R)-2-((5Z,8Z,11Z,14Z,17Z)-icosa-5,8,11,14,17-pentaenylthio)butanoyl)-4-methyl-5-phenyloxazolidin-2-one (1.40 g, 2.55 mmol) in tetrahydrofuran (15 mL) and water (5 mL) held at 0° C. under nitrogen. The reaction mixture was stirred at 0° C. for 45 minutes. 10% Na$_2$SO$_{3(aq)}$ (35 mL) was added, pH was adjusted to ~2 with 5M HCl and the mixture was extracted twice with heptane (35 mL). The combined organic extract was dried (Na$_2$SO$_4$), filtered and concentrated. The residue was subjected to flash chromatography on silica gel using increasingly polar mixtures of heptane and ethyl acetate (98:8→1:1) as eluent. Concentration of the appropriate fractions afforded 0.17 g (22% yield) of the title product as an oil. $^1$H-NMR (300 MHz, CDCl$_3$): δ 1.00 (t, 3H), 1.07 (t, 3H), 1.46 (m, 2H), 1.60-1.75 (m, 3H), 1.85 (m, 1H), 2.10 (m, 4H), 2.66 (m, 2H), 2.80-2.90 (m, 8H), 3.21 (t, 1H), 5.35-5.45 (m, 10H); MS (electrospray): 389.3 [M–H]$^-$; [ ]$_D$, +50° (c=0.14, ethanol).

Example 10: Preparation of ethyl 2-((5Z,8Z,11Z,14Z,17Z)-icosa-5,8,11,14,17-pentaenylthio)-2-methylpropanoate

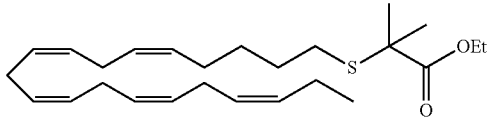 [SMILES: CC/C=C\C/C=C\C/C=C\C/C=C\C/C=C\CCCCSC(C)(C)C(=O)OCC]

To a solution of (5Z,8Z,11Z,14Z,17Z)-icosa-5,8,11,14,17-pentaene-1-thiol (305 mg, 1.00 mmol) in dry DMF (10 mL) at 0° C. under inert atmosphere was added NaH (60% in mineral oil, 44 mg, 1.1 mmol). After fifteen minutes, ethyl 2-bromo-2-methylbutyrate (154 μL, 1.05 mmol) was added and the mixture was stirred for 1.5 hour at 0° C. The reaction mixture was quenched by addition of sat. aq. NH$_4$Cl (20 mL). Water (20 mL) and heptane (50 mL) were added and the phases were separated. The water phase was extracted with heptane (2×25 mL). The combined organics were washed with water (25 mL) and brine (2×25 mL), dried (MgSO$_4$), filtered and evaporated to give 377 mg of the title compound as a crude oil. Purification by flash chromatography on silica gel using isocratic elution (heptane:EtOAc 98:2) afforded 307 mg (77% yield) of the title compound as oil. $^1$H-NMR (300 MHz, CDCl$_3$): δ 0.95 (t, 3H), 1.28 (t, 3H), 1.42 (m, 2H), 1.48 (s, 6H), 1.54 (m, 2H), 2.06 (m, 4H), 2.58 (m, 2H), 2.71-2.85 (m, 8H), 4.15 (m, 2H), 5.22-5.48 (m, 10H); MS (Cl (CH$_4$)): 459 [M+C$_3$H$_5$]$^+$, 447 [M+C$_2$H$_5$]$^+$, 419 [M+H]$^+$, 373 [M-OEt]$^+$, 345 [M-CO$_2$Et]$^+$, 303 [R-S]$^{*+}$.

Example 11: Preparation of 2-((5Z,8Z,11Z,14Z,17Z)-icosa-5,8,11,14,17-pentaenylthio)-2-methylpropanoic acid

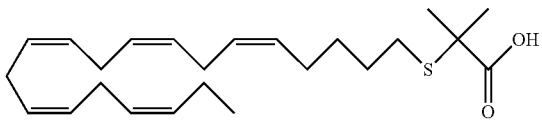 [SMILES: CC/C=C\C/C=C\C/C=C\C/C=C\C/C=C\CCCCSC(C)(C)C(=O)O]

Ethyl 2-((5Z,8Z,11Z,14Z,17Z)-icosa-5,8,11,14,17-pentaenylthio)-2-methylpropanoate (209 mg, 0.50 mmol) was dissolved in ethanol (2.5 mL) and added to a solution of LiOH×H$_2$O (168 mg, 4.0 mmol) in water (2.5 mL). The resulting turbid solution was stirred at 70° C. under inert atmosphere for 2 hours, cooled and added water (10 mL) and 1 M HCl (5 mL) to pH=1-2. The mixture was extracted three times with heptane (3×20 mL). The combined organic extracts were dried (MgSO$_4$), filtered and concentrated under reduced pressure to give 101 mg of the title compound as crude oil. Purification by flash chromatography on silica gel using gradient elution (starting with pure heptane and increasing stepwise to heptane:EtOAc (with 5% HOAc) 80:20) afforded 78 mg (40%) of the title compound as oil. $^1$H-NMR (300 MHz, CDCl$_3$): δ 0.95 (t, 3H), 1.35-1.66 (m, 4H), 1.50 (s, 6H), 2.07 (m, 4H), 2.63 (t, 3H), 2.70-2.92 (m, 8H), 5.13-5.50 (m, 10H).

Example 12: Preparation of ethyl 1-((5Z,8Z,11Z,14Z,17Z)-icosa-5,8,11,14,17-pentaenylthio)cyclobutanecarboxylate

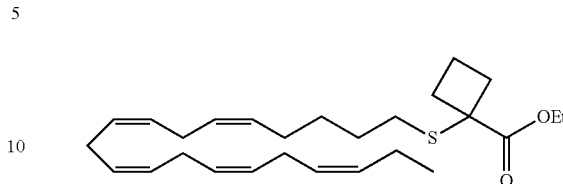

To a solution of (5Z,8Z,11Z,14Z,17Z)-icosa-5,8,11,14,17-pentaene-1-thiol (305 mg, 1.00 mmol) in dry DMF (10 mL) at 0° C. under inert atmosphere was added NaH (60% in mineral oil, 44 mg, 1.1 mmol). After fifteen minutes ethyl 2-bromo-cyclobutane carboxylate (170 μL, 1.05 mmol) was added and the mixture was stirred for 1.5 hour at 0° C. The reaction was quenched by addition of sat. aq. NH$_4$Cl (20 mL). Heptane (50 mL) was added, and the phases were separated. The water phase was extracted with heptane (2×25 mL). The combined organics were washed with water (25 mL) and brine (25 mL), dried (MgSO$_4$), filtered and evaporated to give 409 mg of the title compound as a crude oil. Purification by flash chromatography on silica gel using isocratic is elution (heptane:acetone 98:2) afforded 243 mg (56% yield) of the title compound as oil. $^1$H-NMR (300 MHz, CDCl$_3$): δ 0.95 (t, 3H), 1.27 (t, 3H), 1.42 (d, 3H), 1.54 (m, 2H), 1.84 (m, 1H), 1.96-2.23 (m, 7H), 2.51 (m, 2H), 2.60 (m, 2H), 2.73-2.90 (m, 8H), 4.18 (m, 2H), 5.23-5.43 (m, 10H); MS (Cl (CH$_4$)): 471 [M+C$_3$H$_5$]$^+$, 459 [M+C$_2$H$_5$]$^+$, 431 [M+H]$^+$, 385 [M-OEt]$^+$, 357 [M-CO$_2$Et]$^+$, 303 [R-S]$^{*+}$.

Example 13: Preparation of 2-ethyl-2-((5Z,8Z,11Z,14Z,17Z)-icosa-5,8,11,14,17-pentaenylthio)butanoic acid (Compound N)

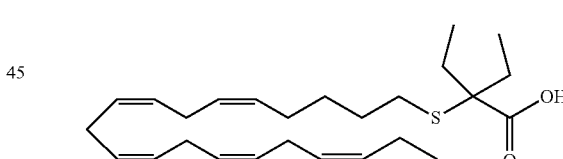

NaOEt (21 wt. % in EtOH, 0.37 mL, 0.98 mmol) was added dropwise to a solution of 2-mercapto-2-ethyl butyric acid (0.08 g, 0.49 mmol) in dry EtOH (7 mL) held at 0° C. under inert atmosphere. The resulting mixture was stirred at 0° C. for 30 minutes before a solution of (5Z,8Z,11Z,14Z,17Z)-icosa-5,8,11,14,17-pentaenyl methanesulfonate (0.15 g, 0.41 mmol) in dry EtOH (3 mL) was added dropwise. The resulting turbid mixture was stirred at ambient temperature for 24 hours, poured into NH4Cl (sat.) (aq.) (15 mL), added 3M HCl to pH ~2 before extracted twice with EtOAc (2×20 mL). The combined organic extracts were washed with brine (10 mL), dried (MgSO4), filtrated and evaporated in vacuo. The residue was purified by flash chromatography on silica gel using a gradient of 10-25% ethyl acetate in heptane as eluent. Concentration of the appropriate fractions afforded 0.12 g (70% yield) of the title compound as oil. 1H-NMR (300 MHz, CDCl$_3$): δ 0.88-1.02 (m, 9H), 1.45-1.58 (2×m, 4H), 1.72 (m, 2H), 1.82 (m, 2H) 2.09 (m, 4H), 2.53 (t, 2H), 2.76-2.86 (m, 8H), 5.29-5.39 (m, 10H. MS (electrospray): 417.3 [M−H]−.

BIOLOGICAL EXAMPLES

Evaluation of Compound N in a Diet Induced NAFLD/NASH Mouse Model (APOE*3Leiden.CETP Double Transgenic Mice)

The APOE*3Leiden.CETP double transgenic mouse is expressing a variant of the human apolipoprotein E3 (APOE3), the APOE*3Leiden, in addition to the human apolipoprotein C1 (APOC1) and CETP. APOE*3Leiden.CETP double transgenic mice exhibit elevated plasma cholesterol and triglyceride levels, mainly confined to the VLDL/LDL sized lipoprotein fraction. By increasing the cholesterol content of the diet in this model, all the characteristics of human NASH develop.

Studies were performed in APOE*3Leiden.CETP mice placed on a high fat diet (24% fat w/w) with varying cholesterol content (0.25-1% cholesterol w/w). In one study (using 1% cholesterol w/w), after a 3 weeks run-in period 17 (20%) low-responder mice were removed from the study and the remaining 65 mice were sub-divided into groups of 12 mice each (+5 in the control group), matched for plasma cholesterol, triglycerides, blood glucose, body weight and age (t=0) and treatment was started. The mice received a daily gavage between 07 hr00 and 10 hr00 with either Compound N, Reference A or control (corn oil). After 4, 8, 12, 16 and 20 weeks of treatment blood samples were taken after a 5 hour fasting period (also 5 hours after compound or vehicle administration). Plasma cholesterol and triglycerides were measured. After 14 weeks of treatment 5 representative mice from the control group were sacrificed in order to assess the NASH development and to determine the termination of the study. After 20 weeks of treatment mice were sacrificed by CO2 asphyxiation, heparin heart blood was sampled and tissues were collected. Hepatic steatosis, inflammation and collagen content were analyzed.

A further study was performed in APOE*3Leiden.CETP mice with a 4-week active treatment arm in mice placed on a high fat diet (24% fat and 0.25% cholesterol diet, both ver/w) to collect additional metabolic data.

Biological Example 1. Effects of Compound N on Hepatic Cholesterol Content

Compound N administered to ApoE*3L-CETP mice (0.25% cholesterol diet mu) induced a significant decrease in hepatic cholesterol ester ($p<0.001$). A mild decrease in cholesterol ester was also observed with Reference A ($p<0.05$). A 43% reduction in total hepatic cholesterol (statistics not performed). The effects of Compound N on hepatic cholesterol are shown in Table 1 and FIG. 1.

TABLE 1

| | Liver lipids (µg lipid/mg liver protein), AVG ± SD | |
|---|---|---|
| Compound | Free cholesterol (FC in FIG. 1) | Cholesterol ester (CE in FIG. 1) |
| Control | 12.3 ± 3.0 | 22.7 ± 5.9 |
| Reference A | 9.5 ± 1.3 | 17.0 ± 3.7 |
| Compound N | 9.8 ± 1.2 | 10.6 ± 2.1 |

Biological Example 2. Effects of Compound N on Hepatic Inflammation

Figure 2:
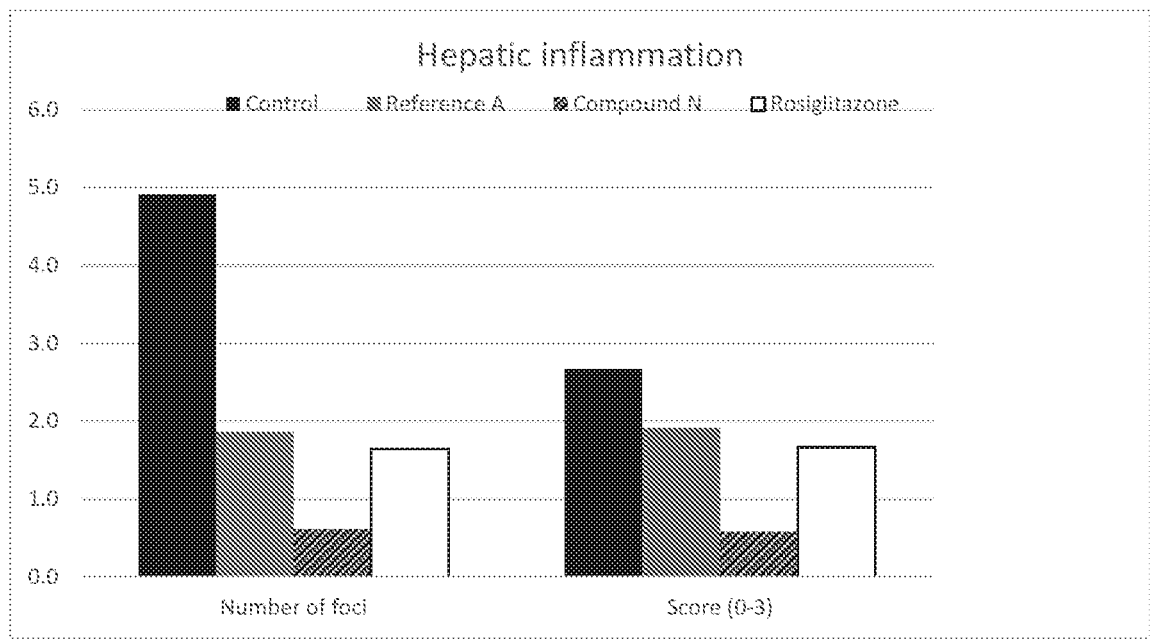
FIG. 2 discloses the effects of Compound N on hepatic inflammation.

Compound N administered to ApoE*3L-CETP mice induced a significant ($p<0.001$) reduction in the number of inflammatory foci by approximately 85%, leading to a significant reduction in the total inflammation score. Reference A induced a milder reduction in inflammatory foci ($p<0.01$). Compound N has a significantly better effect upon hepatic inflammation than Reference A ($p<0.01$). The effects of Compound N on hepatic inflammation are shown in Table 2 and FIG. 2.

TABLE 2

| | Inflammation (number of foci and inflammation score), Mean ± SD. | |
|---|---|---|
| Compound | Number of foci | Score (0-3) |
| Control | 4.9 ± 2.9 | 2.7 ± 0.9 |
| Reference A | 1.9 ± 1.3 | 1.9 ± 1.2 |
| Compound N | 0.6 ± 0.6 | 0.6 ± 0.8 |
| Rosiglitazone | 1.6 ± 1.6 | 1.7 ± 1.2 |

Biological Example 3. Effects of Compound N on Macrovesicular Steatosis

Figure 3:
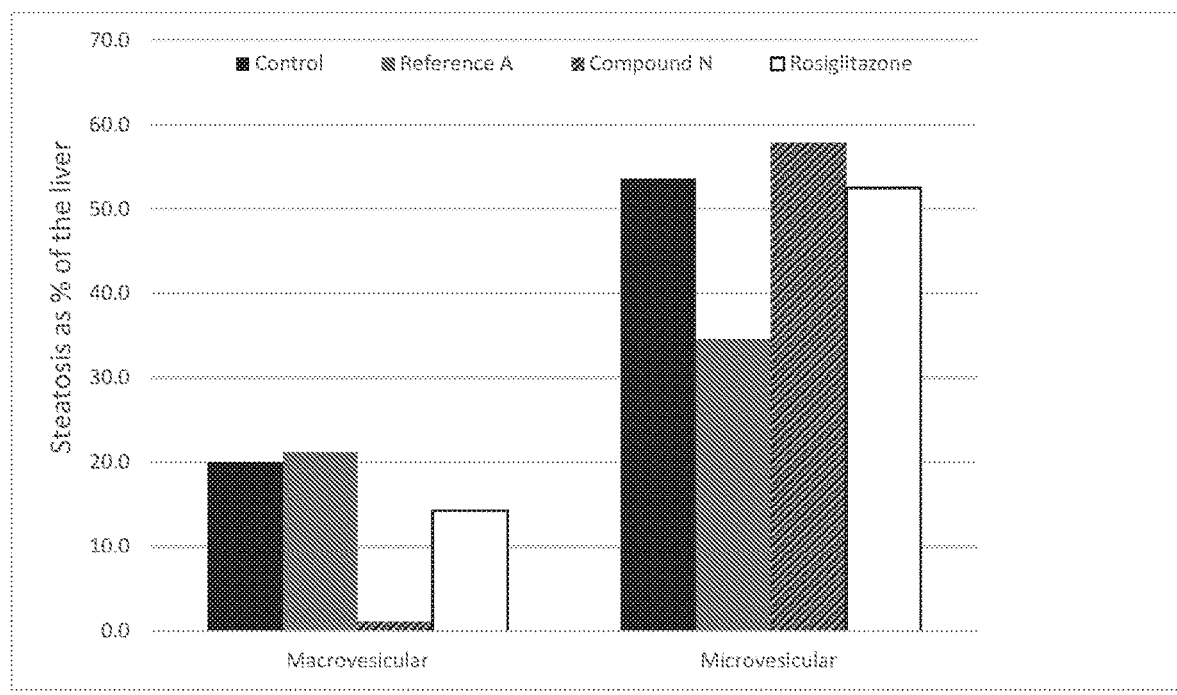
FIG. 3 discloses the effects of Compound N on macrovesicular steatosis.

Compound N administered to ApoE*3L-CETP mice abolished macrovesicular steatosis ($p<0.001$ vs. control). No significant effect upon macrovesicular steatosis was seen with Reference A or Rosiglitazone. Compound N was significantly different from Reference A and Rosiglitazone (both <0.001). The effects of Compound N on macrovesicular steatosis are shown in Table 3 and FIG. 3.

TABLE 3

| | Steatosis as % of the liver (Macrovesicular and microvesicular steatosis), Mean ± SD. | |
|---|---|---|
| | Steatosis as % of the liver | |
| Compound | Macrovesicular | Microvesicular |
| Control | 20.0 ± 15.2 | 53.6 ± 24.1 |
| Reference A | 21.2 ± 15.0 | 34.6 ± 11.8 |
| Compound N | 1.1 ± 1.0 | 57.9 ± 25.4 |
| Rosiglitazone | 14.3 ± 20.2 | 52.5 ± 18.4 |

Biological Example 4. Effects of Compound N on Fecal Bile Acid Content

Figure 4:
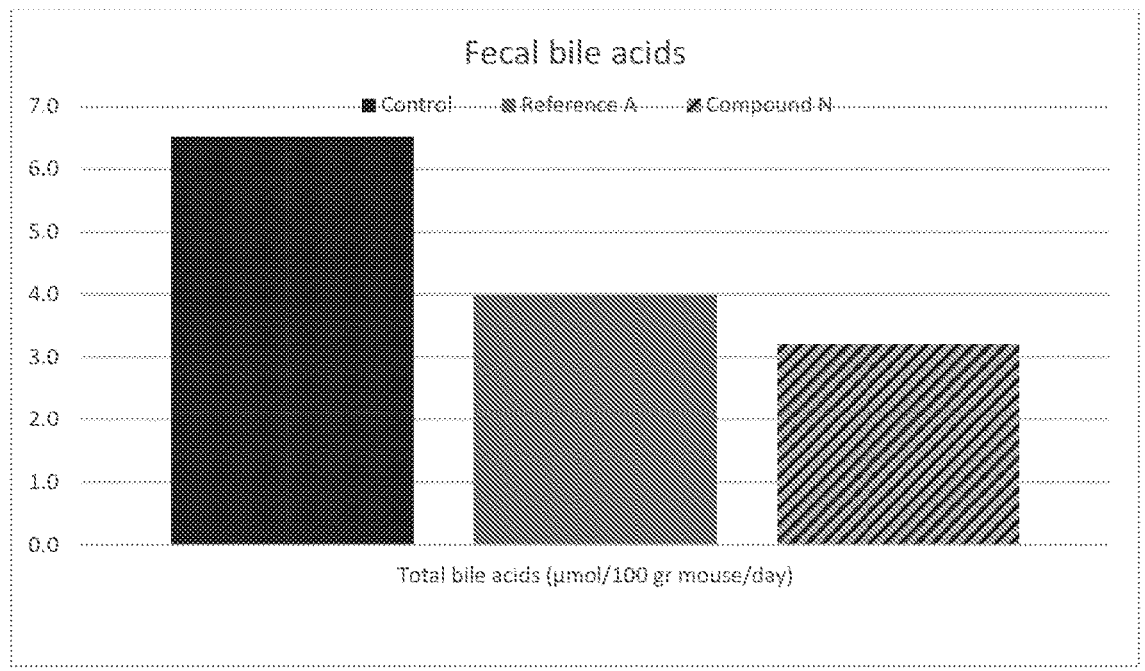
FIG. 4 discloses the effects of Compound N on fecal bile acid content.

Compound N administered to ApoE*3L-CETP double transgenic mice demonstrated a significant ($p=0.006$ vs. control) 50% reduction in fecal bile acid excretion. Reference A induced a milder yet significant decrease ($p<0.05$ vs. control). The Effects of Compound N on fecal bile acid content are shown in Table 4 and FIG. 4.

TABLE 4

| Total bile acids (µmol/100 gr mouse/day), AVG ± SD. | |
|---|---|
| Compound | Total bile acids (µmol/100 gr mouse/day) |
| Control | 6.5 ± 1.9 |
| Reference A | 4.0 ± 1.2 |
| Compound N | 3.2 ± 0.6 |

Biological Example 5. Effects of Compound N on Hepatic Fibrosis (Collagen Content)

Figure 5:
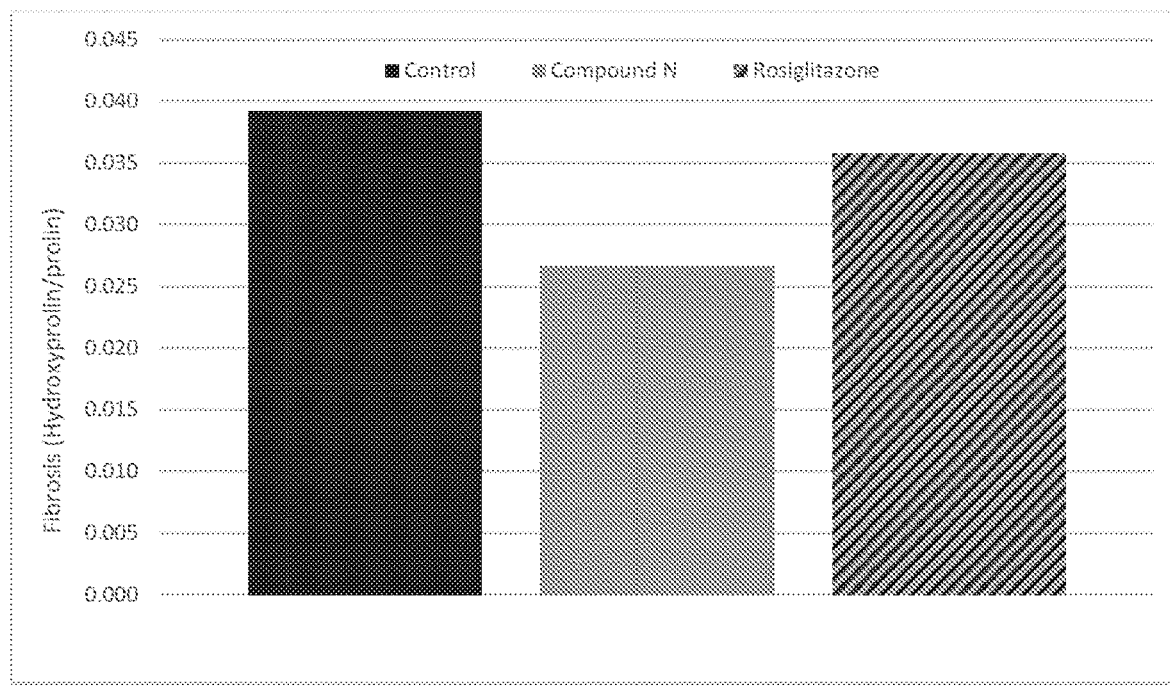
FIG. 5 discloses the effects of Compound N on hepatic fibrosis (collagen content).

Compound N administered to ApoE*3L-CETP double transgenic mice showed a significant (p<0.005) 30% reduction in hepatic collagen content compared to control animals. The effects of Compound N on hepatic fibrosis are shown in Table 5 and FIG. 5.

TABLE 5

Fibrosis (hydroxyprolin/prolin), Mean ± SD.

| Compound | Hydroxyprolin/Prolin |
| --- | --- |
| Control | 0.039 ± 0.010 |
| Compound N | 0.027 ± 0.007 |
| Rosiglitazone | 0.036 ± 0.007 |

Biological Example 6. Effects of Compound N on Total Plasma Cholesterol

Figure 6:
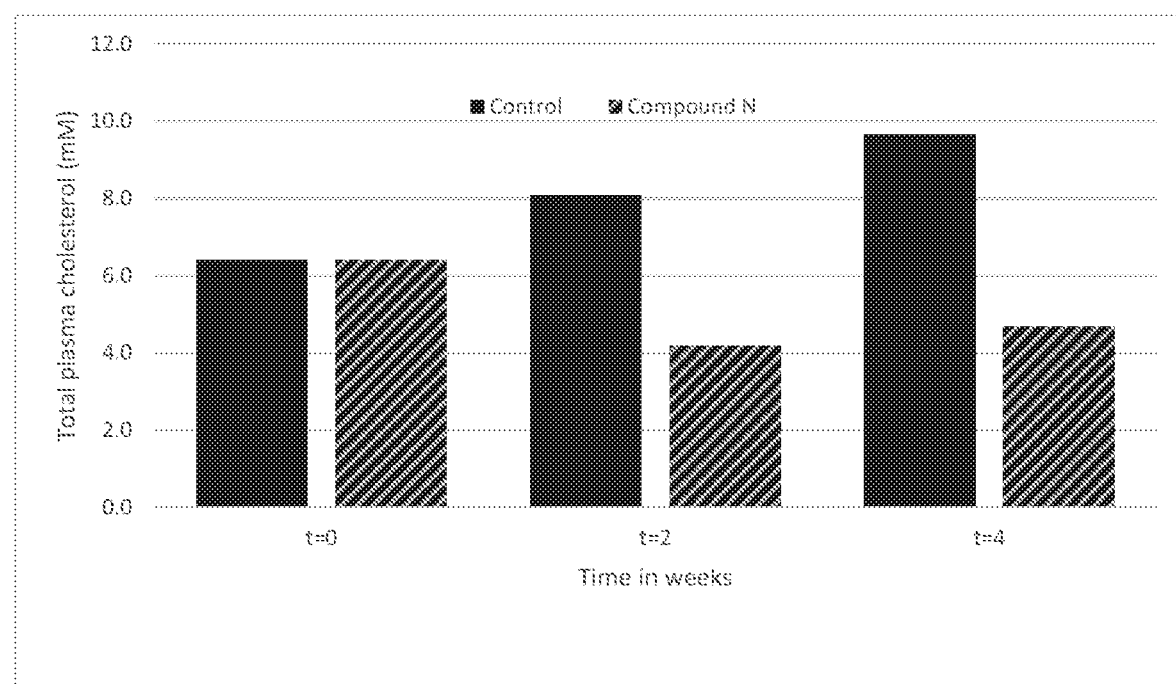
FIG. 6 discloses the effects of Compound N on total plasma cholesterol.

Compound N administered to ApoE*3L-CETP double transgenic mice demonstrated a 52% reduction in total plasma cholesterol after 4 weeks versus control (p<0.001). Plasma HDL cholesterol values were adoubled (p<0.001, data not shown), underlying the fact that the reduction in plasma cholesterol was specific to the atherogenic apoB particle associated cholesterol fraction. The effects of Compound N on total plasma cholesterol are shown in Table 6 and FIG. 6.

TABLE 6

Total plasma cholesterol (mM) as a function of time in weeks, AVG ± SD.

| | Cholesterol (mM) | | |
| --- | --- | --- | --- |
| Compound | t = 0 | t = 2 | t = 4 |
| Control | 6.4 ± 1.5 | 8.1 ± 1.8 | 9.7 ± 2.6 |
| Compound N | 6.4 ± 1.1 | 4.2 ± 0.7 | 4.7 ± 1.3 |

The invention claimed is:

1. A method for reducing hepatic cholesterol in a subject having non-alcoholic steatohepatitis, wherein the method comprises administering to the subject in need thereof a pharmaceutical composition comprising at least one pharmaceutically acceptable excipient and a pharmaceutically effective amount of a compound of Formula (I):

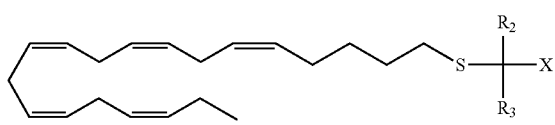

Formula (I)

or a pharmaceutically acceptable salt or enantiomer thereof, wherein:
$R_2$ is H, $C_1$-$C_6$ alkyl, or $C_3$-$C_6$ cycloalkyl;
$R_3$ is H, $C_1$-$C_6$ alkyl, or $C_3$-$C_6$ cycloalkyl; and
X is C(O)OH or C(O)O$C_1$-$C_6$ alkyl;
with the proviso that $R_2$ and $R_3$ are not simultaneously H.

2. The method according to claim 1, wherein X is C(O)OH.

3. The method according to claim 1, wherein:
$R_2$ is $CH_2CH_3$; and
$R_3$ is $CH_2CH_3$.

4. The method according to claim 1, wherein:
$R_2$ is $CH_2CH_3$;
$R_3$ is $CH_2CH_3$; and
X is C(O)OH.

5. The method according to claim 1, wherein the method comprises administering a pharmaceutical composition comprising from 5 mg to 2 g of the compound of Formula (I).

6. The method according to claim 1, wherein the method comprises administering a pharmaceutical composition comprising from 200 mg to 800 mg of the compound of Formula (I).

7. The method according to claim 1, wherein the pharmaceutical composition further comprises an antioxidant selected from the group consisting of butylated hydroxyanisole, butylated hydroxytoluene, and tocopherol, or a mixture thereof.

8. A method for reducing fecal bile content in a subject having non-alcoholic steatohepatitis, wherein the method comprises administering to the subject in need thereof a pharmaceutical composition comprising at least one pharmaceutically acceptable excipient and a pharmaceutically effective amount of a compound of Formula (I):

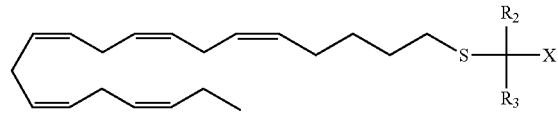

Formula (I)

or a pharmaceutically acceptable salt or enantiomer thereof, wherein:
$R_2$ is H, $C_1$-$C_6$ alkyl, or $C_3$-$C_6$ cycloalkyl;
$R_3$ is H, $C_1$-$C_6$ alkyl, or $C_3$-$C_6$ cycloalkyl; and
X is C(O)OH or C(O)O$C_1$-$C_6$ alkyl;
with the proviso that $R_2$ and $R_3$ are not simultaneously H.

9. The method according to claim 8, wherein X is C(O)OH.

10. The method according to claim 8, wherein:
$R_2$ is $CH_2CH_3$; and
$R_3$ is $CH_2CH_3$.

11. The method according to claim 8, wherein:
$R_2$ is $CH_2CH_3$;
$R_3$ is $CH_2CH_3$; and
X is C(O)OH.

12. The method according to claim 8, wherein the method comprises administering a pharmaceutical composition comprising from 5 mg to 2 g of the compound of Formula (I).

13. The method according to claim 8, wherein the pharmaceutical composition further comprises an antioxidant selected from the group consisting of butylated hydroxyanisole, butylated hydroxytoluene, and tocopherol, or a mixture thereof.

14. A method for reducing hepatic inflammation and hepatic steatosis in a subject having non-alcoholic steatohepatitis, wherein the method comprises administering to the subject in need thereof a pharmaceutical composition comprising at least one pharmaceutically acceptable excipient and a pharmaceutically effective amount of a compound of Formula (I):

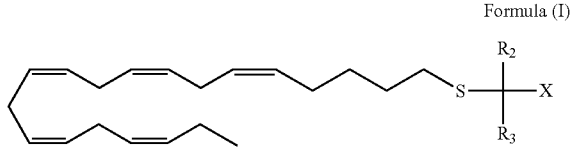

Formula (I)

or a pharmaceutically acceptable salt or enantiomer thereof, wherein:
$R_2$ is H, $C_1$-$C_6$ alkyl, or $C_3$-$C_6$ cycloalkyl;
$R_3$ is H, $C_1$-$C_6$ alkyl, or $C_3$-$C_6$ cycloalkyl; and
X is C(O)OH or C(O)O$C_1$-$C_6$ alkyl;
with the proviso that $R_2$ and $R_3$ are not simultaneously H.

15. The method according to claim 14, wherein X is C(O)OH.

16. The method according to claim 14, wherein:
$R_2$ is $CH_2CH_3$; and
$R_3$ is $CH_2CH_3$.

17. The method according to claim 14, wherein:
X is C(O)OH;
$R_2$ is $CH_2CH_3$; and
$R_3$ is $CH_2CH_3$.

18. The method according to claim 14, wherein the method comprises administering a pharmaceutical composition comprising from 5 mg to 2 g of the compound of Formula (I).

19. The method according to claim 14, wherein the method comprises administering a pharmaceutical composition comprising from 200 mg to 800 mg of the compound of Formula (I).

20. The method according to claim 14, wherein the pharmaceutical composition further comprises an antioxidant selected from the group consisting of butylated hydroxyanisole, butylated hydroxytoluene, and tocopherol, or a mixture thereof.

* * * * *